(12) United States Patent
Konrad

(10) Patent No.: US 7,188,734 B2
(45) Date of Patent: Mar. 13, 2007

(54) HOLDING DEVICE, PARTICULARLY FOR BODILY FLUIDS, COMPRISING A SEPARATING DEVICE, AND A SEPARATING DEVICE THEREFOR

(75) Inventor: Franz Konrad, Schwanenstadt (AT)

(73) Assignee: Greiner Bio-One GmbH, Kremsmünster (AT)

( * ) Notice: Subject to any disclaimer, the term of this patent is extended or adjusted under 35 U.S.C. 154(b) by 372 days.

(21) Appl. No.: 10/473,553

(22) PCT Filed: Mar. 28, 2002

(86) PCT No.: PCT/AT02/00095

§ 371 (c)(1),
(2), (4) Date: Sep. 29, 2003

(87) PCT Pub. No.: WO02/078848

PCT Pub. Date: Oct. 10, 2002

(65) Prior Publication Data

US 2004/0217046 A1  Nov. 4, 2004

(30) Foreign Application Priority Data

Mar. 30, 2001 (AT) .................... A 512/2001
Aug. 3, 2001 (AT) ..................... A 1210/2001
Mar. 25, 2002 (AT) .................... A 455/2002

(51) Int. Cl.
*B01D 21/26* (2006.01)
*B65D 39/14* (2006.01)
*B01L 3/14* (2006.01)

(52) U.S. Cl. ............ 210/516; 210/513; 210/518; 215/247; 215/274; 220/200; 220/916; 422/101; 422/102

(58) Field of Classification Search ........... 210/513, 210/516, 518; 422/101, 102; 215/247, 274; 220/200, 916
See application file for complete search history.

(56) References Cited

U.S. PATENT DOCUMENTS

| | | | |
|---|---|---|---|
| 3,779,383 A | * 12/1973 | Ayres | ............ 210/789 |
| 3,849,072 A | 11/1974 | Ayres | |
| 3,897,337 A | 7/1975 | Ayres | |
| 3,897,340 A | 7/1975 | Ayres | |
| 3,897,343 A | 7/1975 | Ayres | |
| 4,202,769 A | 5/1980 | Greenspan | |
| 4,443,345 A | * 4/1984 | Wells | ............ 210/782 |
| 4,464,254 A | 8/1984 | Dojki et al. | |
| 5,266,199 A | 11/1993 | Tsukagoshi et al. | |

(Continued)

FOREIGN PATENT DOCUMENTS

AT            402365        4/1997

(Continued)

*Primary Examiner*—John Kim
(74) *Attorney, Agent, or Firm*—Collard & Roe, P.C.

(57) ABSTRACT

A separating mechanism for inserting in a receptacle chamber of a container receptacle having a longitudinal axis comprises two adjacently disposed components and a sealing device which is directed towards an internal wall of the container receptacle. The components have two ends spaced apart from one another in the direction of the longitudinal axis, and a flow passage extends therebetween. The components can be applied against the internal wall by at least one pressing element and, in an initial position, the flow passage is established between the adjacently disposed components spaced apart from one another by the pressing element.

44 Claims, 19 Drawing Sheets

U.S. PATENT DOCUMENTS

| | | | |
|---|---|---|---|
| 5,275,299 A | 1/1994 | Konrad et al. | |
| 5,495,958 A | 3/1996 | Konrad et al. | |
| 5,522,518 A | 6/1996 | Konrad et al. | |
| 5,871,700 A | 2/1999 | Konrad et al. | |
| 6,277,331 B1 * | 8/2001 | Konrad | 422/102 |
| 6,406,671 B1 * | 6/2002 | DiCesare et al. | 422/101 |
| 6,516,953 B1 * | 2/2003 | DiCesare et al. | 210/516 |

FOREIGN PATENT DOCUMENTS

| | | |
|---|---|---|
| DE | 4132480 | 4/1993 |
| DE | 19513453 | 10/1995 |
| DE | 19835721 | 2/2000 |
| EP | 0311011 | 4/1989 |
| EP | 0419490 | 11/1993 |
| EP | 0445 707 | 8/1995 |
| EP | 0735921 | 11/1996 |
| EP | 0753741 | 1/1997 |
| EP | 0974373 | 1/2000 |
| EP | 1005910 | 6/2000 |
| EP | 1006360 | 6/2000 |
| EP | 1106250 | 6/2001 |
| EP | 1106251 | 6/2001 |
| EP | 1106252 | 6/2001 |
| EP | 1106253 | 6/2001 |
| EP | 1107002 | 6/2001 |
| WO | WO9605770 | 2/1996 |

* cited by examiner

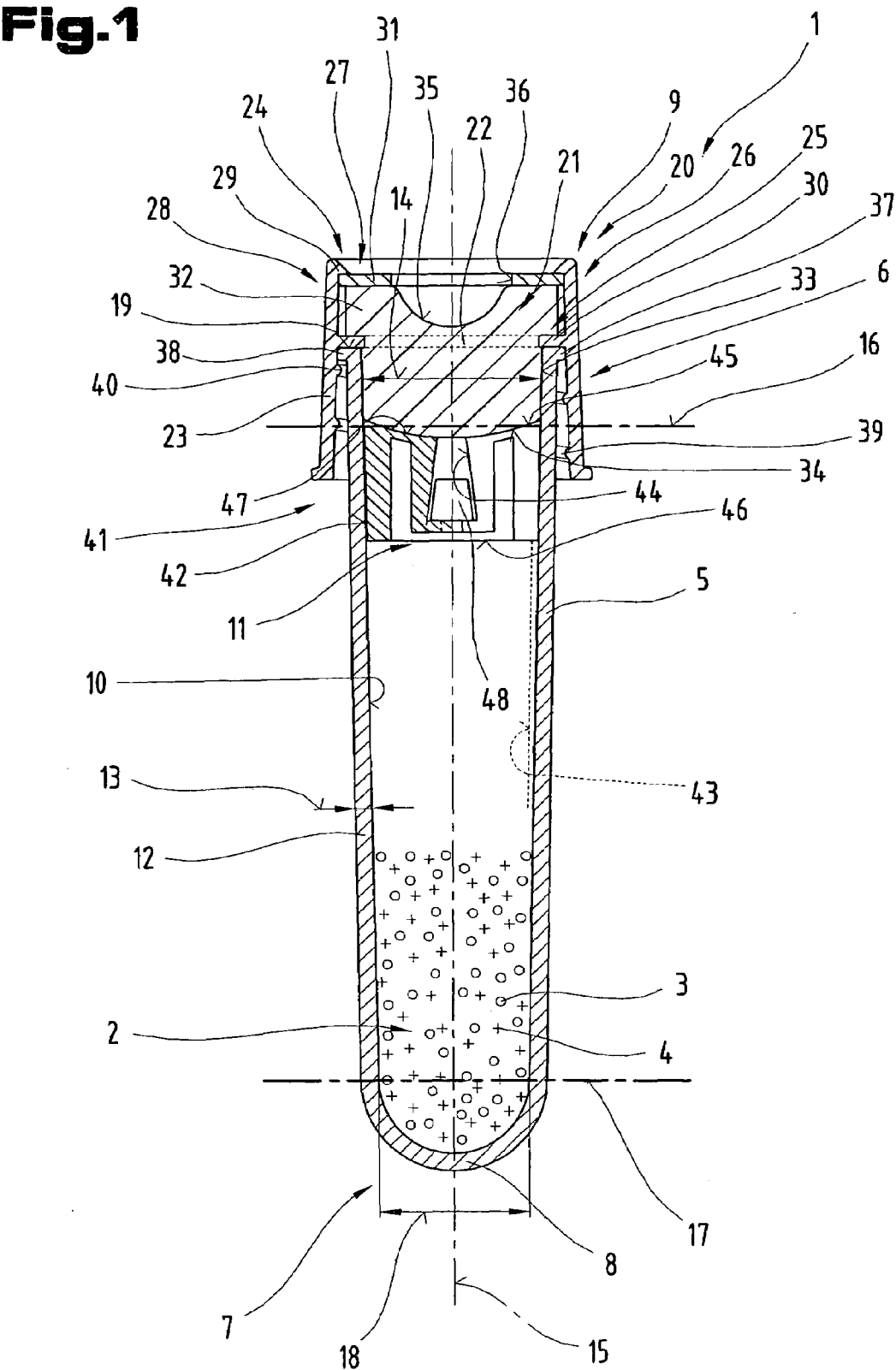

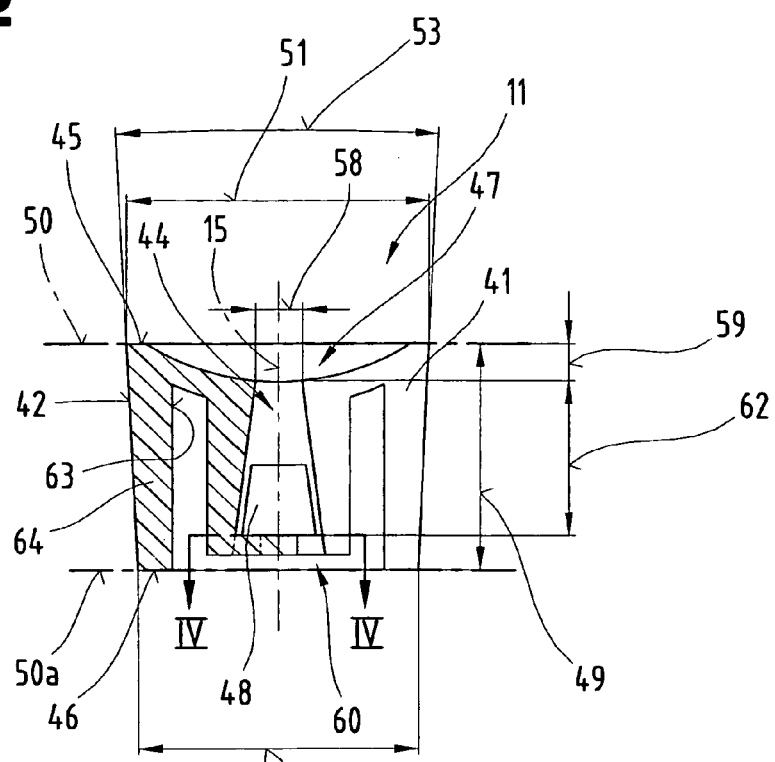
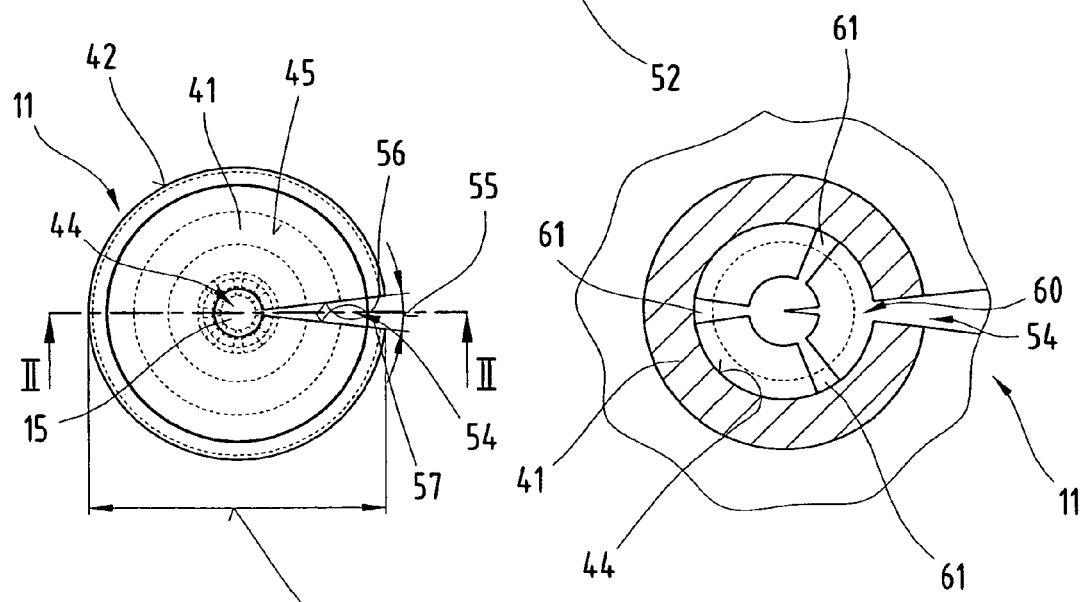

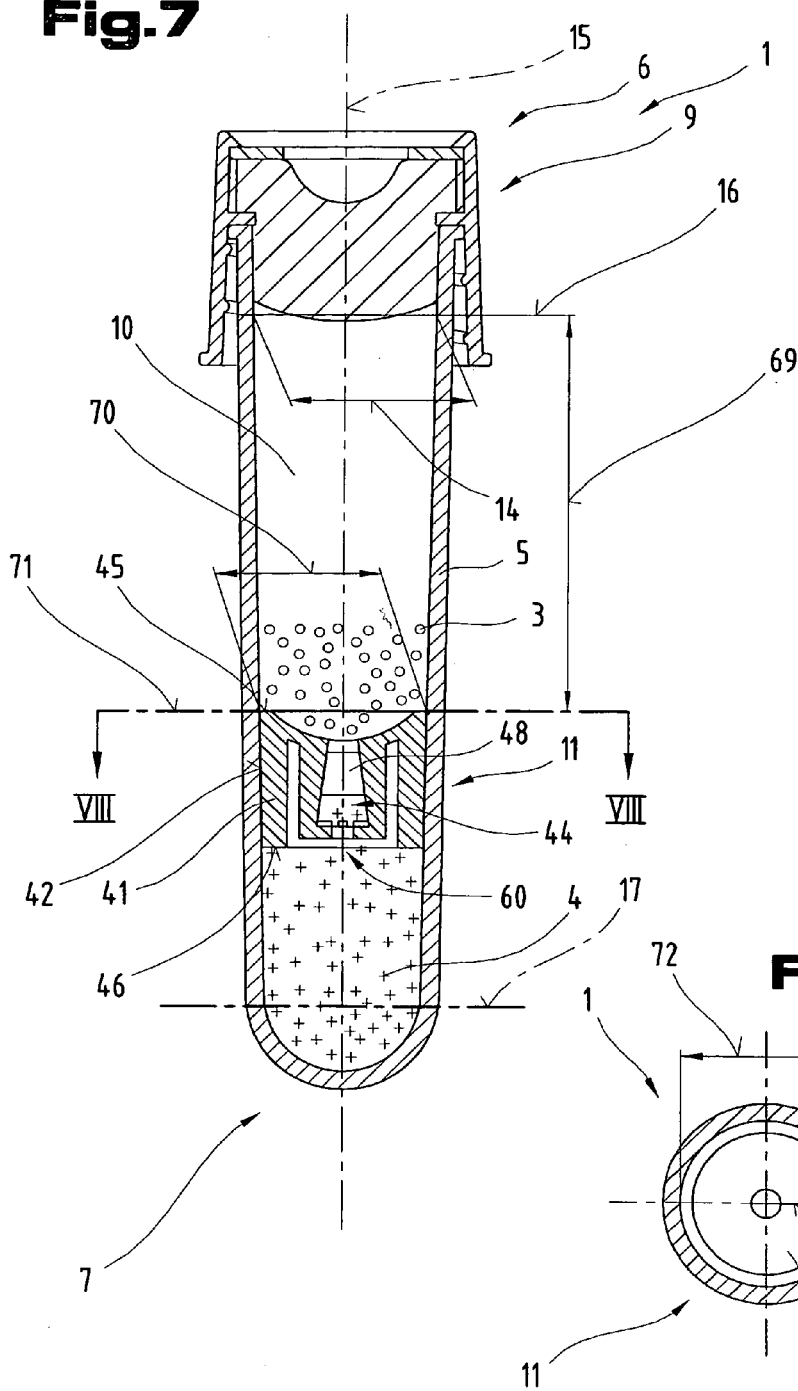
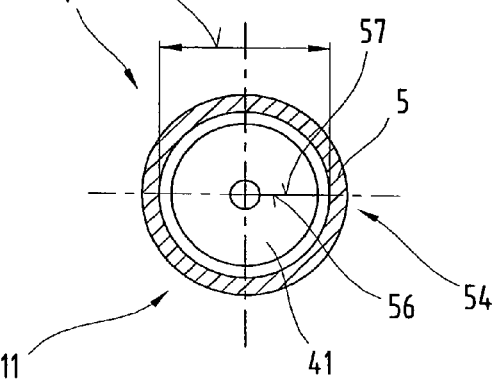

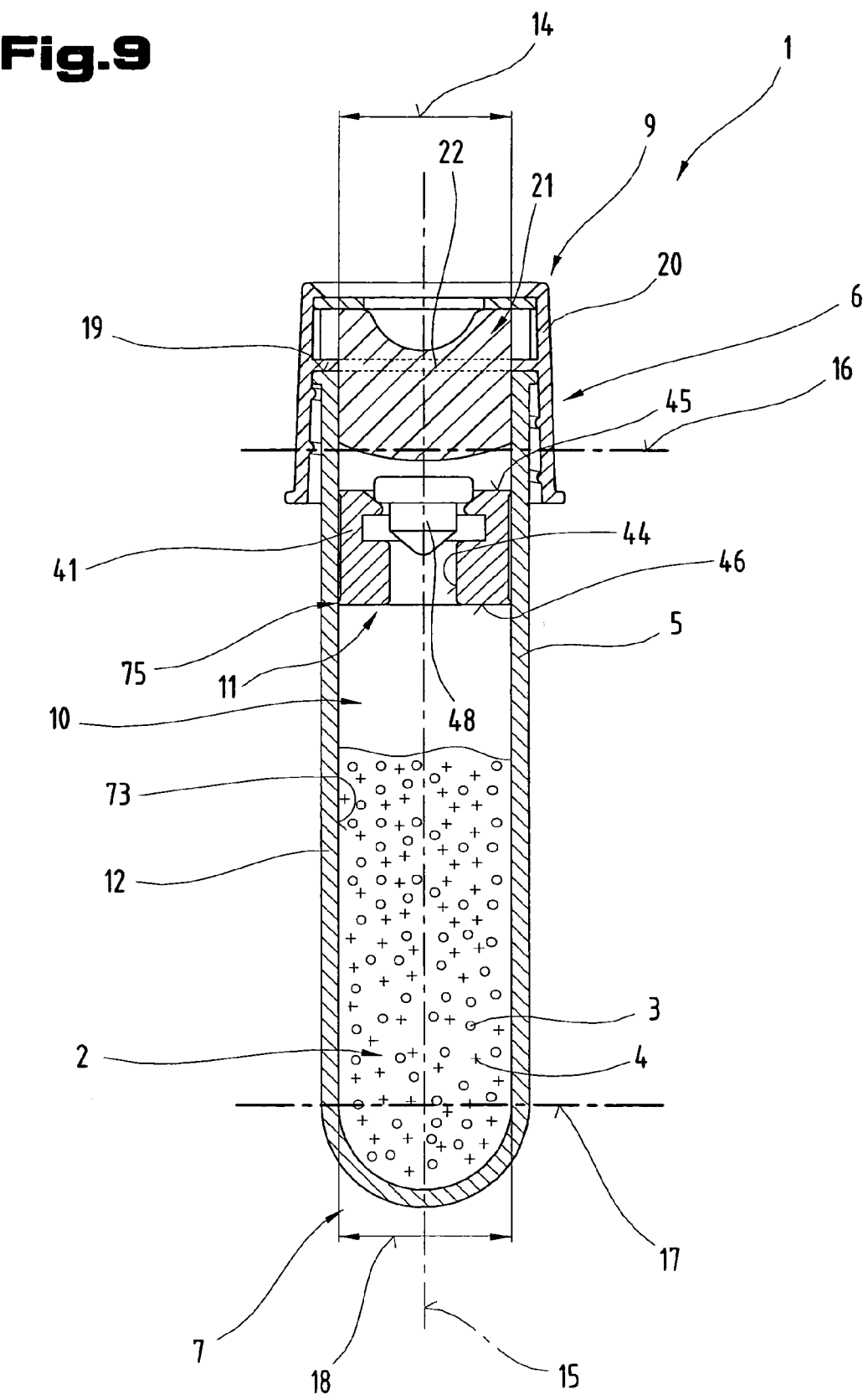

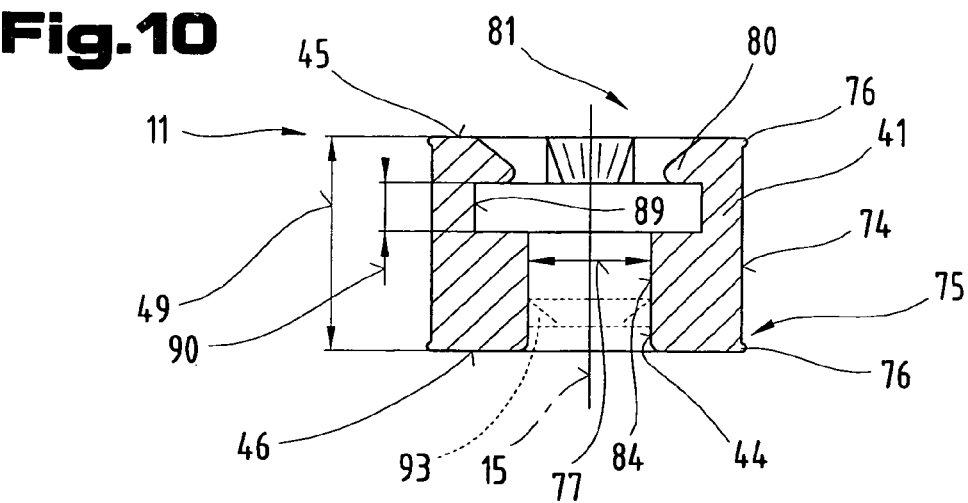
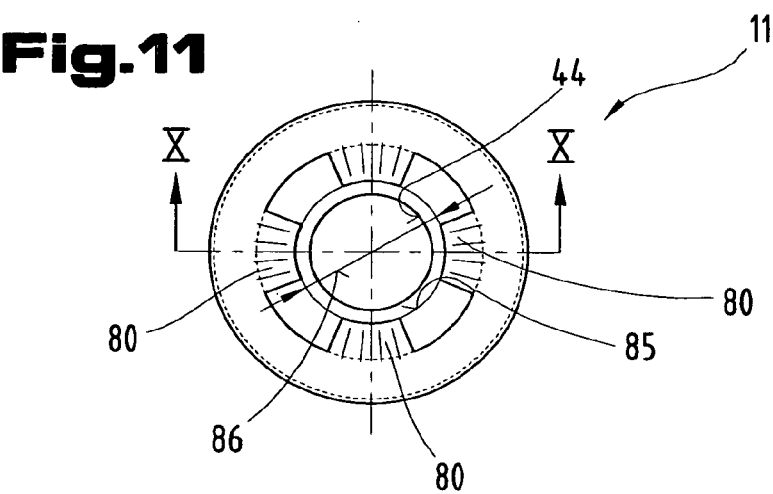
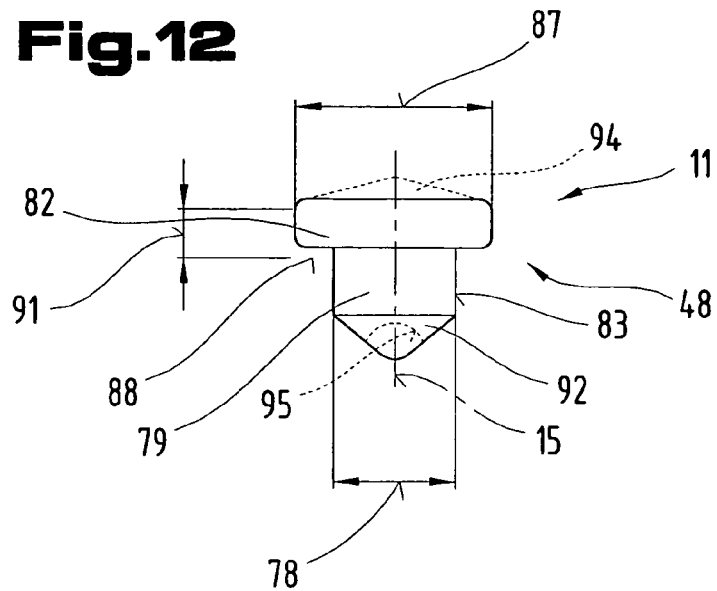

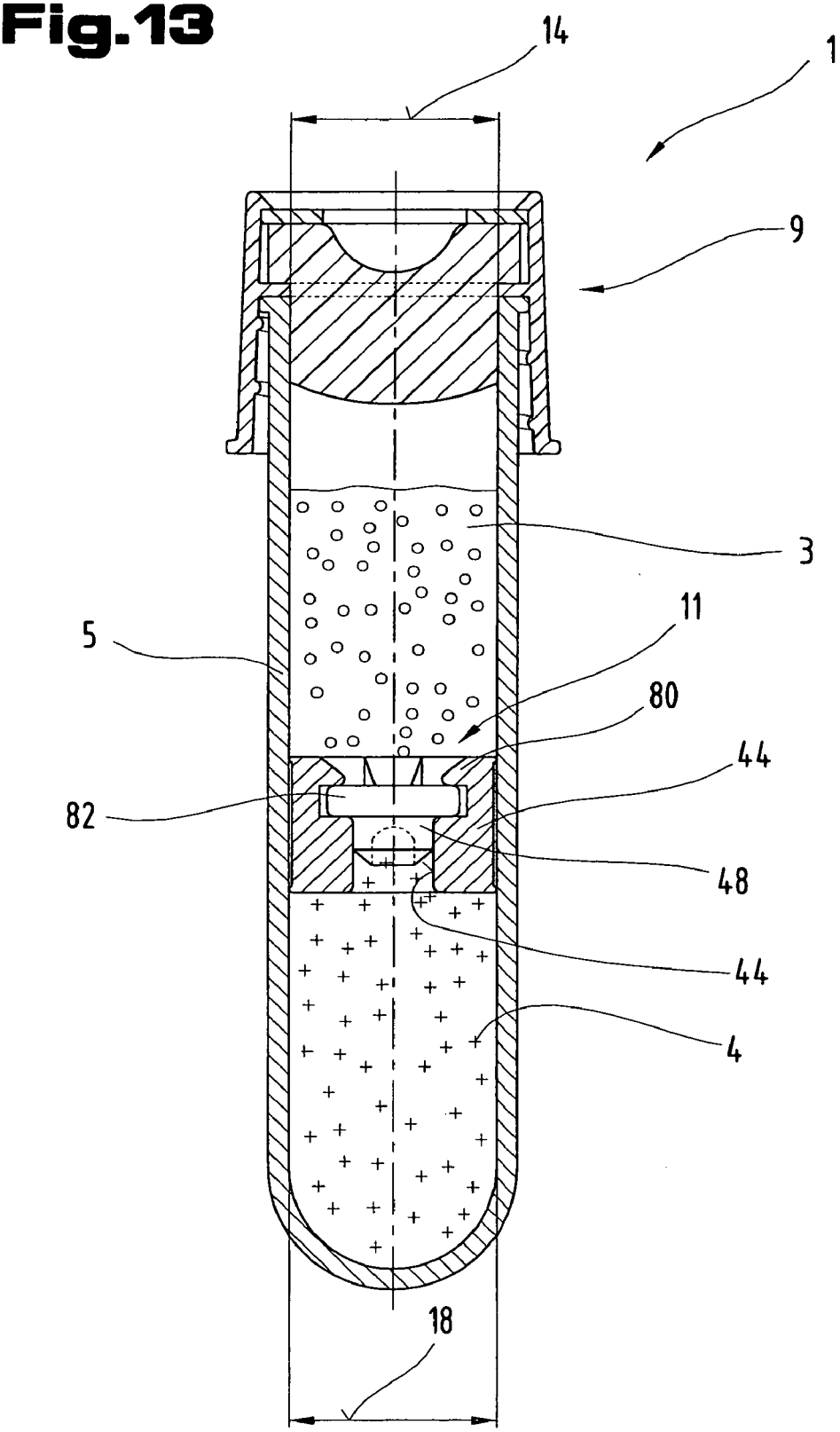

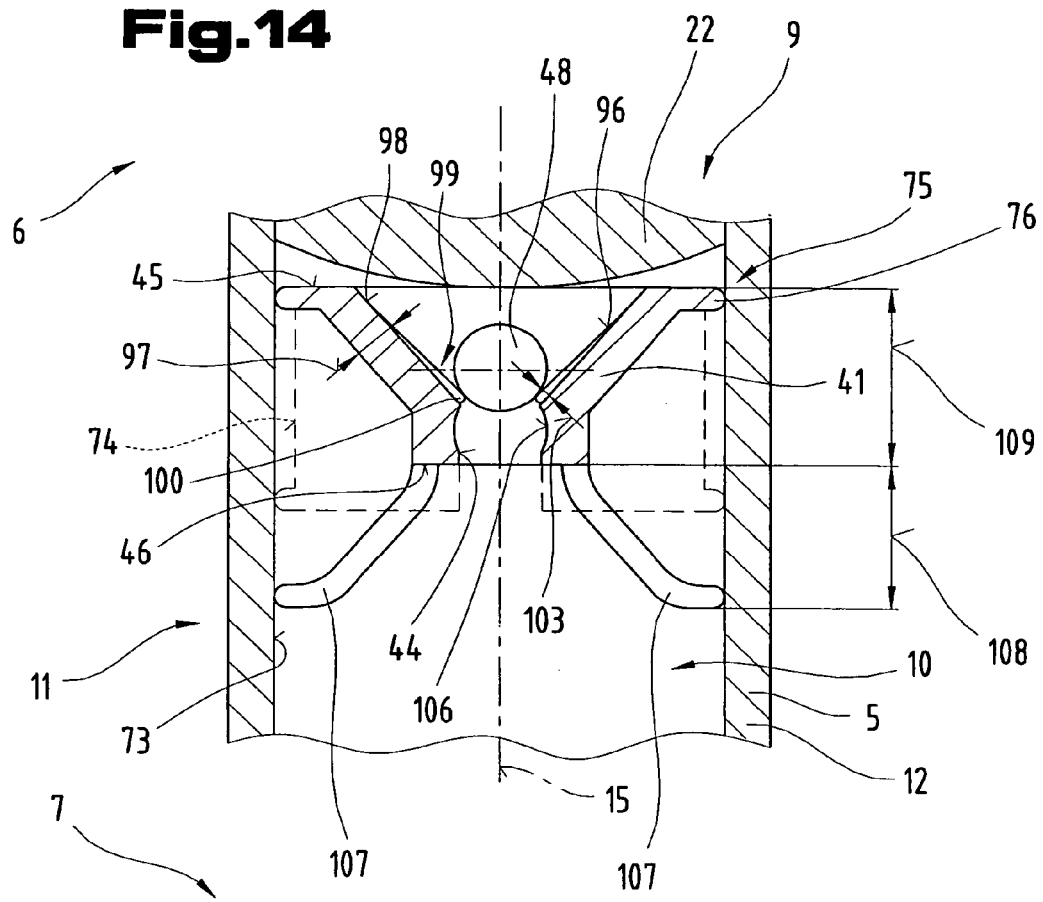

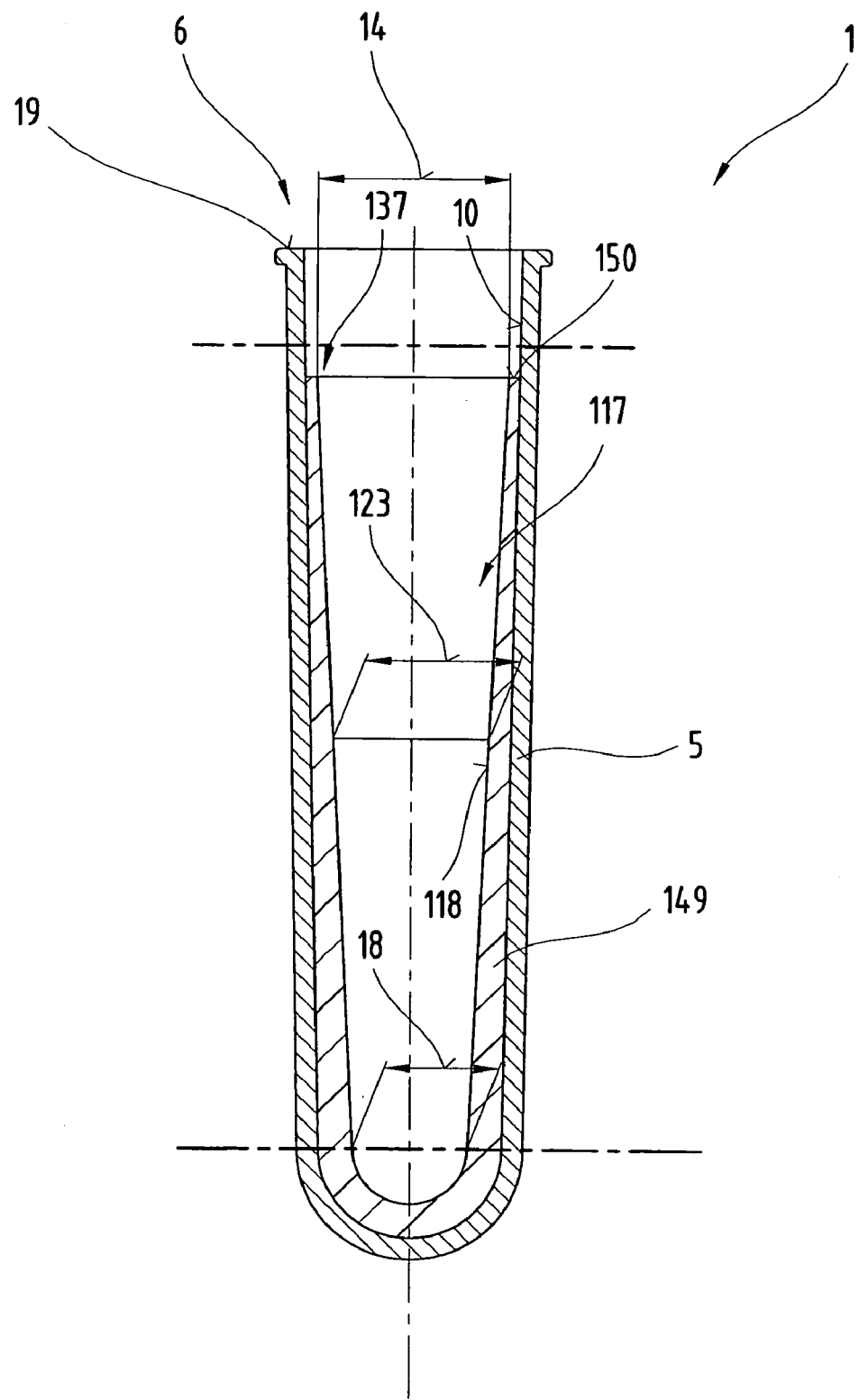

HOLDING DEVICE, PARTICULARLY FOR BODILY FLUIDS, COMPRISING A SEPARATING DEVICE, AND A SEPARATING DEVICE THEREFOR

CROSS REFERENCE TO RELATED APPLICATIONS

Applicants claim priority under 35 U.S.C. §119 of Austrian Applications No. A512/2001 filed on Mar. 30, 2001, A 1210/2001 filed on Aug. 3, 2001, and A 455/2002 filed on Mar. 25, 2002. Applicants also claim priority under 35 U.S.C. §365 of PCT/AT02/00095 filed on Mar. 28, 2002. The international application under PCT article 21(2) was not published in English.

The invention relates to a separating mechanism for inserting in the interior of a container system and a container system incorporating such a separating mechanism.

A separation mechanism for inserting in a receptacle chamber of a container receptacle of a container system is known from patent specification U.S. Pat. No. 5,266,199 A and has an elastic support body surrounded by an elastic ring with a separation in its peripheral region and a ball which can be inserted in a flow passage inside the elastic support body to provide a seal. The purpose of the elastic ring surrounding the elastic support body is to provide a sealing mechanism between the internal wall of the container receptacle and the elastic support body when the separating mechanism is in the inserted position. The flow passage through the elastic support body, which extends between the two end regions spaced apart from one another in the direction of a longitudinal axis, is closed off by the ball floating on the higher-density constituents in the usage position.

A container system with a container receptacle is known from patent specification EP 0 753 741 A1, which has two ends spaced apart from one another in a longitudinal axis, at least one of which has an orifice. The internal dimension of the container receptacle in the region of the first open end in the plane perpendicular to the longitudinal axis is bigger than the internal dimension in the region of the other end in the plane parallel therewith in the same spatial direction. An annular component is inserted in the open end and covers the open end face of the container receptacle with a collar, and a cylindrical wall part projects into the interior of the container receptacle, at least in certain regions. Adjoining the cylindrical wall part, the annular component has a shoulder and a cross-sectional widening joined to it, on which the elastic sealing element of the separating device is supported in the initial position. The separating mechanism has a recess at the centre, which is closed off by a thin cover plate in the region of the top end of the container receptacle. The individual components are assembled, and in particular the separating mechanism inserted, in a vacuum chamber, because the interior can no longer be accessed without causing damage once the separating mechanism has been inserted. A film is also bonded onto the collar-shaped shoulder of the annular component and a cap applied. The interior is filled by piercing the thin cover plate of the separating mechanism, the thin film and optionally the cap. As a result of this filling process, there is no longer a vacuum in the interior and air is sucked into the interior. This is followed by the centrifugation process, during which the separating mechanism moves out of the annular component towards the closed end and sits with its sealing element on the internal surface of the container receptacle. The settling speed in the mixture or the separated constituents is determined by the contact force of the elastic sealing element on the internal surface. As a result the density selected for the separating mechanism as a whole relative to the constituents contained in the mixture to be separated, the latter floats at the boundary surface between the two media, each being of a differing density. During the centrifugation process, the lighter medium is able to get between the internal surface of the container receptacle and the elastic sealing element.

Another container system with a separating mechanism is known from patent specification EP 1 005 910 A2 and has a cylindrical container receptacle with a virtually constant internal diameter. A sealing system which can be pierced is provided at the open end of the container receptacle, against which the separating mechanism sits in virtual abutment, including in the initial position. This separating mechanism is made from a flexible, rebounding material and a seal is provided on the outer periphery of the separating mechanism to seal the internal surface of the container receptacle. Another deformable element is also inserted in the interior, which is forced against the internal wall of the outer container by the pressure exerted by the medium when subjected to centrifugal force, forming a flow passage between the separating mechanism and the inserted, deformed insert part which assumes a sealing position in conjunction with the seals disposed on the separating mechanism once the centrifugal force is halted, as a result of which the media which have been separated from one another remain separated.

Another container system for a mixture of at least two media is known from patent specification DE 195 13 453 A1, with a container receptacle of the test tube type closed off by a sealing mechanism at an open end region, in which a separating mechanism is inserted to keep the different media of the mixture separate after the separation process. In order to prevent the end face of the separating mechanism, which comes into contact with only one medium, from being contaminated when the interior of the container is filled with the mixture, the separating mechanism has an orifice in the middle region, through which the mixture can be introduced into the rest of the interior of the container. During the subsequent separation process, which is by conventional centrifugation with a radial centrifugal force (rcf) of 1,000 g to 5,000 g—where g represents the force of gravity and 1 g has a value of 9.81 m/s$^2$—one of the media separated from the mixture is transferred through the orifice in the separating mechanism into the region located between the sealing mechanism and the separating mechanism and, as a results, drops to the closed end of the container. In order to prevent another medium contained between the closed end and the separating mechanism from getting through the orifice after the separation process and being able to mix back with the media separated from it, a conical end stop widening towards the closed end is provided at a height corresponding to the standard remaining amount of the other medium, by means of which the separating mechanism runs on the end stop, which penetrates the orifice. Immediately at the point where the external diameter of the end stop corresponds to the internal diameter of the orifice, the separating mechanism stays put in this position so that the orifice is closed off by the shoulder, thereby preventing any further exchange or any further mixing between the two media. The disadvantage of this embodiment is that it is necessary to make a tube with a stop inside and there is no guarantee that the function of keeping the media separate will work reliably due to the fact that an orifice is provided in the separating mechanism.

Furthermore, the separating mechanism has to be inserted in the interior of the container subsequently and this is a somewhat complex process.

Other container systems for centrifuging mixtures of at least two media in order to separate them are known from patent specification WO 96/05770 A1 and in this case the container is provided with a sealing device at both end regions. A separating mechanism affording a seal is provided in the interior and is formed by a gel. During the centrifugation process, this plug of gel migrates due to its specific weight, which is higher than the specific weight of the medium having the lower specific weight and is lower than the medium with the higher specific weight, because of the centrifugal forces acting on it between the two different media separated from one another. Once positioned in this manner, one medium can then be separated from the other medium of the mixture. The disadvantage of this system is that because the separating mechanism is a gel, the period for which it can be stored is not long enough for the normal period of use in many instances.

Other container systems incorporating separating mechanisms, which have a range of different valve systems and filter elements, are also known from patent specifications EP 0 311 011 A2, U.S. Pat. Nos. 3,897,343 A, 3,897,340 A, 4,202,769 A and 3,897,3

Yet other container systems incorporating separating mechanisms are disclosed in patent specifications EP 1 106 250 A2, EP 1 106 251 A2, EP 1 106 252 A2, EP 1 106 253 A2 and EP 1 107 002 A2, in which various embodiments are used for the separating mechanisms, based on the principle whereby one component of the separating mechanism is deformable during the centrifugation process and is acted due to the ratio of density between the media to be separated.

The underlying objective of the present invention is to propose a separating mechanism and a container system incorporating such a separating mechanism, by means of which the constituents of a mixture to be separated can be kept reliably and permanently separated during the centrifugation process and during the subsequent period of storage.

This object is accomplished according to one aspect of this invention with a separating mechanism for inserting in a receptacle chamber of a container receptacle having a longitudinal axis, comprising at least two adjacently disposed components and a sealing device which is directed towards an internal wall of the container receptacle. The components have two ends spaced apart from one another in the direction of the longitudinal axis, and a flow passage extends therebetween. The components can be applied against the internal wall by at least one pressing element and, in an initial position, the flow passage is established between the adjacently disposed components spaced apart from one another by the pressing element.

The advantage derived from the combination of these features resides in the fact that a separating mechanism of this type can be made as a single component which can be inserted in the interior of the container receptacle, and a passage is provided for one of the constituents to be separated from the mixture until the point at which the operating position is reached. An automatic mechanical abutment or mechanical seating is produced against the internal surface of the container receptacle in the pre-definable position. As a result of this separating mechanism and the mechanical seating, a top head of the constituent separated from the mixture can be removed from between the separating mechanism and the sealing device, which can be opened if necessary, without the separating mechanism slipping towards the closing mechanism, thereby preventing any undesirable mixing of the constituents once they have been separated.

The medium to be separated is always guaranteed to be able to pass through the flow passage, and once the operating position is reached a perfect seal is always guaranteed between the receptacle chambers which have to be kept separate inside the container system if the components are displaced at the same relative speed during their entire displacement motion relative to the container receptacle.

Also of advantage is the embodiment of disposing the pressing element between regions of the components directed towards one another because the components are not able to move relative to one another except perpendicular to the displacing motion, which prevents them from shifting in the direction of the longitudinal axis.

If the components are displaced relative to one another in a plane perpendicular to the longitudinal axis, the components are forced against the respective oppositely lying internal walls of the container, thereby opening up the flow passage until such time as the two components are also sitting one against the other at the mutually facing regions providing a seal.

A uniformly directed pressing force is applied to the components, thereby preventing them from jamming or becoming blocked during the displacement process as a result of the embodiment.

The forces needed to produce the opening motion to form the flow passage are transmitted to the components uniformly, which on the one hand ensures a reliable abutment of the components against the requisite points of the internal walls and on the other guarantees an obstructed flow through the flow passage if the pressing element has V-shaped resilient webs, as viewed in the direction of the longitudinal axis, and coverage in that direction towards , or remote from, the longitudinal axis, for instance two such webs converging remote from the longitudinal axis, with facing ends joined to one another, or if the pressing element is comprised of the complementary curved resilient webs, as viewed in the direction of the longitudinal axis, disposed in a plane substantially perpendicular to the flow passage and joined at facing end regions which may or may not be provided with a circular connecting part.

The flow passage can be reliably sealed, including in the region where the components abut with one another, if an appropriate recess is provided in order to accommodate the pressing element in at least one of facing regions of the components.

A sealing system for sealing off the flow passage is advantageously provided between the components of the separating mechanism in the area of the end of the components directed towards a first end of the container receptacle to enable an even more reliable seal to be obtained between the receptacle chambers confining the media to be separated.

Dead spaces in the area around the separating mechanism are avoided, thereby providing a complete separation, without any risk of one of the media becoming contaminated subsequently, if the sealing device is disposed between the separating mechanism and the receptacle chamber in the area of a first end of the components directed towards a first end of the container receptacle.

The sealing device is advantageously comprised of at least one sealing lip extending continuously around the periphery of the components, whereby the separating mechanism sits in abutment with the internal wall of the container in the region of sealing lips only, which thereby enables any manufacturing tolerances which might occur to be compensated.

A reliable seal is also provided between the mutually separated receptacle chambers in the region of the flow passage directed towards the container if sections of the sealing lips adjacent to the flow passage overlap at least when the separating mechanism is in an operating position.

Advantageously, several support elements are provided on the components projecting out from the external surface thereof in the direction remote from the longitudinal axis. Thus, the components are prevented from being applied against large surface areas of the internal walls of the container. This simultaneously produces a sufficient guiding action during the entire displacement process until the tight seating is obtained. The friction force needed to achieve the tight seating is also increased because the surface area available for the abutment is significantly smaller which means that manufacturing tolerances can be more easily compensated.

The components of the separating mechanism are advantageously pivotably linked by a hinge joint engaging around the peripheral region thereof and the flow passage, which on the one hand provide a connection between the components and on the other provide the functions of the pressing element and support element. This means that only a small number of components is needed.

If a retaining mechanism for the separating mechanism is inserted in the receptacle chamber in the form of a web projecting out from at least certain regions of the periphery of the internal wall in the direction towards the longitudinal axis, the constituents of the mixture to be separated can be reliably prevented from sticking to the separating mechanism and its components.

According to another aspect of the invention, there is provided a container receptacle which bounds a receptacle chamber with an internal wall and has two ends spaced apart in the direction of the longitudinal axis of the container receptacle, at least one of the ends having an orifice. An internal dimension of the receptacle chamber in the region of a first one of the ends in a plane perpendicular to the longitudinal axis is bigger than an internal dimension in the region of a second one of the ends in a plane parallel therewith. The container system comprises at least one closing device for the end having the orifice, and a separating mechanism inserted in the receptacle chamber and displaceable from an initial position to an operating position spaced apart in the direction towards the second end. The separating mechanism comprises at least two components applied by at least one pressing element against certain regions of the internal wall of the container receptacle. The internal dimension and an internal periphery of an envelope line of the receptacle chamber in the plane perpendicular to the longitudinal axis is bigger than an external dimension and an external periphery of an envelope line of the components in the operating position, and a flow passage is established between the ends in the region of the separating mechanism in the initial position. An internal dimension and an internal periphery of an envelope line of the receptacle chamber in the region of the operating position is the same as or smaller than the external periphery of an envelope line of the components in the same position. The components of the separating mechanism automatically seal off the flow passage in the operating position.

The advantage of this approach is that at least one flow passage, which can be closed off, is established between the mutually spaced apart end regions of the separating mechanism and this passage is maintained in both directions by at least one pressing element in the region of its initial position up until the point at which the operating position is reached because the pressing element pushes the separating mechanism, which may be made from at least one component, against certain regions of the internal wall of the container receptacle. As a result of the fact that the container receptacle becomes constantly smaller towards the closed end, in conjunction with the distance between the components and between them and the container receptacle, a mechanical tight seating or tight clamping of the separating mechanism on the internal surface of the container is obtained after a pre-definable displacement path because of the dimensions. This tight seating or tight clamping action occurs when the component or components close off the flow passage and the internal dimension of the container receptacle in the region of the operating position of the separating mechanism is the same as or smaller than the external periphery of the component in the same position. This constant reduction of the flow passage is achieved by a constant taper in the interior of the container receptacle, which acts in the manner of a control curve, completely closing off the flow passage. The displacing motion is brought about by the centrifugal force acting on the separating mechanism, which on the one hand initiates a separation process so that the mixture is separated into its individual constituents, and on the other produces the displacing motion until the point at which the separating mechanism and the container receptacle are mechanically blocked. In this respect, the extent of the displacement path in the direction of the longitudinal axis can be fixed by the size selected for the flow passage in the region of the initial position and the extent of the taper in the interior. As a result of the design of the separating mechanism, the separating mechanism may be assembled and inserted in the interior, after which it can be evacuated and sealed by the sealing device, because it is always possible to gain access to the closed end through the separating mechanism. Consequently, filling can proceed unobstructed and the separating mechanism does not have to be inserted subsequently, obviating the need to remove the closing device prior to the start of the centrifugation process. This guarantees a high degree of operating safety.

Various advantageous embodiments guarantee a pre-defined retaining force on the separating mechanism inserted in the interior immediately the initial position is assumed, prior to the centrifugation process and hence also during the filling process.

BRIEF DESCRIPTION OF THE DRAWINGS

The invention will be described in more detail with reference to examples of embodiments illustrated in the appended drawings.

Of these:

FIG. 1 is a simplified, schematic diagram in section, showing a side view of a container system proposed by the invention with a separating mechanism disposed in the initial position and a sealing device;

FIG. 2 is a diagram on a larger scale, showing a side view of the separating mechanism illustrated in FIG. 1, viewed in section along line II—II indicated in FIG. 3;

FIG. 3 is a plan view of the separating mechanism illustrated in FIG. 2;

FIG. 4 is a plan view of a part-region of the base body in the region of the connecting orifice, viewed in section along line IV—IV indicated in FIG. 2 and on an enlarged scale;

FIG. 7 shows the container system after the media have been separated and with the separating mechanism in the operating position;

FIG. 8 is a plan view of the separating mechanism in the operating position, seen in section along line VIII—VIII indicated in FIG. 7;

FIG. 9 is a simplified, schematic diagram showing a side view in section of another container system proposed by the invention with a different separating mechanism disposed in the initial position and a sealing device;

FIG. 10 is a simplified diagram on a larger scale, showing a side view in section through the base body of the separating mechanism illustrated in FIG. 9, along line X—X indicated in FIG. 11;

FIG. 11 is a plan view of the base body illustrated in FIG. 10;

FIG. 12 is a side view of the insert part of the separating mechanism illustrated in FIG. 9;

FIG. 13 shows the container system with the separating mechanism illustrated in FIGS. 9 to 12 in its operating position;

FIG. 14 is a simplified, schematic diagram in section, showing a side view of another embodiment of a separating mechanism proposed by the invention in a partially illustrated container system;

FIG. 30 is a simplified, schematic diagram showing a side view in section of another embodiment of the container system proposed by the invention with the sealing device and separating mechanism removed;

Figure 5:
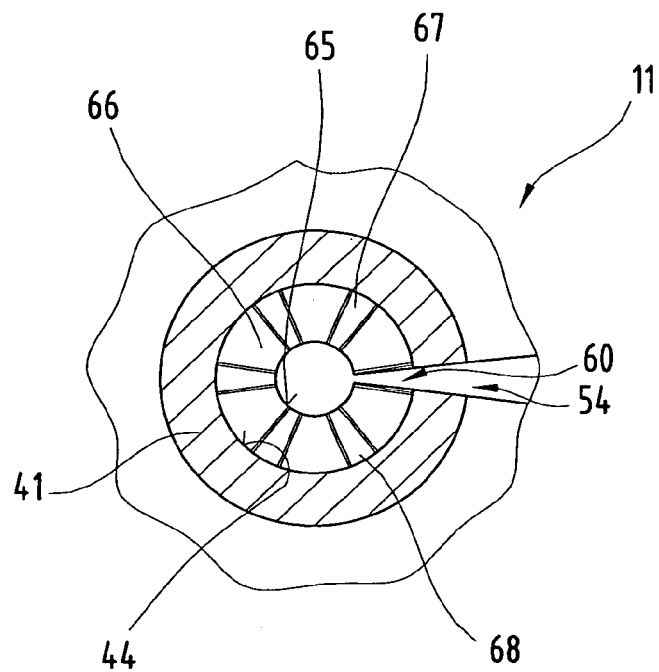
FIG. 5 is plan view of another embodiment of the retaining mechanism in the base body, viewed in section and on an enlarged scale.

Firstly, it should be pointed out that the same parts described in the different embodiments are denoted by the same reference numbers and the same component names and the disclosures made throughout the description can be transposed in terms of meaning to same parts bearing the same reference numbers or same component names. Furthermore, the positions chosen for the purposes of the description, such as top, bottom, side, etc, relate to the drawing specifically being described and can be transposed in terms of meaning to a new position when another position is being described. Individual features or combinations of features from the different embodiments illustrated and described may be construed as independent inventive solutions or solutions proposed by the invention in their own right.

FIGS. 1 to 4 show a container system 1 for a mixture 2 of at least two different constituents or media 3, 4, such as bodily fluids, pieces of tissue or tissue cultures, for example, which is designed in such a way that the mixture 2 contained in the container system 1 can be separated into at least two constituents. This process of separating or dividing the mixture 2 into its constituents or media 3, 4 may be a physical centrifugation process operated in a conventional manner, for example, starting from the non-operating position and reaching a radial centrifugal acceleration of 1,000 g to 5,000 g, preferably 2,200 g, where g represents the gravitational acceleration and the value 1 equals 1 g 9.81 $M/s^2$. As a result, the more solid phase can be split off from the liquid phase and can be separated on the basis of the differing density values, as will be explained in more detail with reference to the drawings below.

The container system 1 consists of a substantially cylindrical container receptacle 5 with two ends 6, 7 spaced at a distance apart from one another, the end 6 in the embodiment illustrated as an example here being open and the end 7 being closed off by an end wall 8. The end 6 which is open in this instance can be closed off if necessary by means of a closing device 9, illustrated in simplified format, and may be of the type disclosed in patent specifications EP 0 445 707 B1, EP 0 419 490 B1, U.S. Pat. Nos. 5,275,299 A, 5,495,958 A and 5,522,518 A, and to avoid repetition, reference may be made to these disclosures with respect to the cap, the sealing device, the housing or container, the coupling mechanism between the cap and the sealing device and the cap and container receptacle 5 and the retaining ring, these publications being included in this application. A separating mechanism 11 is inserted in an interior 10 enclosed by the container receptacle 5, which, in the initial position, is disposed immediately adjacent to the closing device 9. The assembly and mounting process will be described in more detail later. This container receptacle 5 with the closing device 9 may also be used as an evacuated tube for taking blood samples, for which purpose a whole range of embodiments may be used.

The container receptacle 5 may be a bottle, vial, flask or of similar design and may be made from a variety of materials, such as plastic or glass for example. If plastic is selected as the material for the container receptacle 5, it may be a liquid-tight, in particular water-tight, and optionally gas-tight material, such as polyethylene terephthalate (PET), polypropylene (PP), polyethylene (PE), polystyrene (PS), high-density polyethylene (PE-HD), acrylonitrile butadiene styrene copolymers (ABS) or similar or a combination selected from any of these.

The container receptacle 5 also has a container wall 12 with a wall thickness 13, the container wall 12, having an internal dimension 14 in a region extending from the one end 6 in a plane 16 perpendicular to a longitudinal axis 15 between the two ends 6, 7 as far as another plane 17 in the region of the end 7, extending parallel with the first plane 16, where the dimension 18 is smaller. The container wall 12 of the container receptacle 5 has an internal face directed towards the interior 10 and an external face remote therefrom, thereby fixing an external periphery of the container receptacle 5. The internal face of the container wall incorporating the internal height dimensions 14, 18 defines an internal cross section, which cross section may be in a variety of shapes, such as circular, elliptical, oval or polygonal, for example. The shape of the external cross section may also be circular, elliptical, oval, polygonal, etc., and the shape of the external cross section need not necessarily be the same as the shape of the external cross section.

It is of particular advantage if the internal dimension 14 of the container receptacle 5 is designed so that there is a constant slight reduction starting from one end 6 through to the other end 7 spaced at a distance apart from it, terminating with the internal dimension 18, so that if made from a plastic material using an injection moulding process, the container receptacle 5 can be easily de-moulded from the injection moulding tool. Furthermore, this conical taper between the two planes 16, 17 predetermines the extent of the reduction in the internal dimension starting from what is in this case the larger dimension 14 through to the smaller dimension 18. By reference to the oppositely lying internal faces of the container receptacle 5, the taper or conical angle is between 0.1° and 3.0°, preferably between 0.6° and 0.8°. It should be pointed out at this stage that the dimensions described here in relation to the distance between mutually opposite internal and external faces of components, the diameter, the periphery along an enclosing or enveloping line as well as the cross section or cross-sectional surface are given respectively in relation to a plane disposed perpendicular to the longitudinal axis 15 and the same spatial direction is always used for determining the dimensions.

As may also be seen from this diagram, the end 6 has an open end face 19, which may be closed off by the closing device 9, which can then be opened again if necessary. To this end, the closing device 9 consists of a cap 20 enclosing the open end face 19 and a sealing device 21 retained in it, such as a sealing stopper 22 made from a highly elastic and self-closing material which can be pierced, such as pharmaceutical rubber, silicone rubber or bromo-butyl rubber, for example. This cap 20 is disposed so as to be concentric with the longitudinal axis 15 and is provided in the form of a circular cap casing 23. For coupling purposes, means are provided between the cap 20 and the sealing device 21, such as coupling parts 24 to 27 of a coupling mechanism 28, for example, consisting of extensions 29, 30 disposed in certain regions of the internal periphery, optionally with a retaining ring 31, in the case of the cap 20, whilst in the case of the sealing device 21 these consist of a shoulder 32 projecting out from at least certain regions of the external periphery thereof.

In the embodiment illustrated as an example here, the sealing device 21 is provided in the form of the sealing stopper 22 and has a peripheral cylindrical sealing surface 33 which is disposed essentially concentric with the longitudinal axis 15, sitting against the internal face of the container receptacle 5 in the position in which it seals off the portion at the end 6. Accordingly, the internal face of the container receptacle 5 in this region must be of a surface quality which is good enough to serve as a sealing surface. The sealing device 21 also has another sealing surface 34, oriented substantially perpendicular to the longitudinal axis 15, which co-operates with the sealing surface 33 lying against the internal surface in order to close and seal off the interior 10 of the container receptacle 5 from the outside atmosphere at its open end face 19. Providing the extension 30 between the shoulder 32 projecting out from the sealing surface 33 and the open end face 19 of the container receptacle 5 prevents the shoulder 32 from sticking or becoming firmly adhered directly on the end face 19.

On the side directed towards the retaining ring 31, the sealing device 21 also preferably has a recess 35, which essentially has the same cross-sectional surface as an orifice 36, this orifice 36 being dimensioned such that a cannula, not illustrated, can be inserted through it unobstructed so that the sealing device 21 can then be pierced.

The shoulder 32 constituting the coupling part 26, which projects out from the sealing surface 33 of the sealing device 21 in at least part-regions of the periphery in a flange-type arrangement, is retained between the extensions 29 and 30, which are spaced apart from one another in the direction of the longitudinal axis 15 and in planes perpendicular thereto, and are provided in the form of projections or blocks which may be provided at least intermittently or alternatively in a continuous annular arrangement. In order to ensure that the sealing device 21 is securely retained in the cap 20, another option is to insert the retaining ring 31 between the shoulder 32 and the extension 29. This being the case, the retaining ring 31 has a bigger external diameter than an internal dimension between the extensions 29 and 30 in a direction perpendicular to the longitudinal axis 15. Similarly, the diameter of the opening 36 of the retaining ring 31 is smaller than an external dimension of the shoulder 32 in a plane perpendicular to the longitudinal axis 15. However, this external dimension of the sealing device 21 is such that it is bigger than the internal dimension 14 of the internal cross section and hence the interior 10 by at least double the wall thickness 13 of the container receptacle 5. Sine the extension 30 constituting the coupling part 25 has an internal opening width substantially corresponding to the internal dimension 14 of the container receptacle 5 at its top end 6, the shoulder 32 sits very effectively in the cap 20 and a good seal is obtained between the interior 10 of the container receptacle 5 and the atmosphere surrounding the container system 1.

The tightness of the closing device 9 for the open end face 19 of the container system 1 is primarily improved if an external diameter of the sealing device 21 in the region of its sealing surface 33 in the unclamped state outside of the container receptacle 5 is bigger than the internal dimension 14 of the container receptacle in the region directed towards the sealing device 21.

When the shoulder 32 of the sealing device 21 is in the unclamped, non-mounted state, a longitudinal or height extension in the direction of the longitudinal axis 15 is bigger than a distance of a groove-shaped recess between the two extensions 29, 30, less a thickness of the retaining ring 31 where one is provided. As a result of the above dimensional differences between the groove-shaped recess and the lengthwise dimensions of the shoulder 32 and the thickness of the retaining ring 31 in the direction of the longitudinal axis 15, the shoulder 32 is clamped between the two extensions 29, 30. This simultaneously compresses and clamps the sealing device 21 relative to the cap 20 and, where applicable, additionally produces a firm seating for the retaining ring 31, as well as a tight contact between the two end faces of the shoulder 32 in the region of the two extensions 29, 30.

It is also of advantage if the cap casing 23 is designed as a frustoconical or truncated casing, ensuring that the cap casing 23 engages in the region of the top end face 19.

It has also been found to be of practical advantage to provide at least two guide extensions 37, 38 in the region of the open end face 19 of the container receptacle 5, which stand proud of the external periphery of the cylindrical container receptacle 5. However, it would also be possible to provide any other number of guide extensions 37, 38, which will in turn cooperate with guide webs 39, 40 disposed on an internal face of the cap 20 directed towards the container receptacle 5 and standing proud of the surface thereof in the direction towards the longitudinal axis 15. This being the case, the number of guide webs 39, 40, which may be uniformly distributed around the periphery at an angular offset, will depend on the number of guide extensions 37, 38 provided on the container receptacle 5. These guide extensions 37, 38 co-operate with the guide webs 39, 40 disposed on the internal face of the cap casing 23, so that when the cap 20 is pushed in the direction of the longitudinal axis 15 of the container receptacle 5 into the open end face 19 thereof and turned in a clockwise direction, the guide webs 39, 40 run onto the guide extensions 37, 38, thereby enabling the sealing device 21 to be inserted and pushed into the interior 10 of the container receptacle 5 by its sealing surface 33 as the guide webs 39, 40 are guided along the guide extensions 37, 38.

Also illustrated in the interior 10 of the container receptacle 5 is the separating mechanism 11 with its base body 41, which has an abutment face 42 directed towards the container receptacle 5. It is of advantage if the material used for the base body 41 is of the deformable, elastically rebounding type, in which case it may be a silicone rubber, pharmaceutical rubber, rubber, a gel or an elastomer synthetic material, for example. Otherwise, a selection could be made from a range of fluid-tight, in particular water-tight, and optionally gas-tight plastics, for example from the group consisting of polyethylene terephthalate (PET), polypropylene (PP), polyethylene (PE), polystyrene (PS), high-density polyethylene (PE-HD), acrylonitrile butadiene styrene copolymers (ABS) or similar materials or a combination of any of them.

However, it would also be possible to incorporate a whole range of additives in the material in order to obtain an exact adjustment of the pre-definable density. A density should be between 1.02 g/cm$^3$ and 1.07 g/cm$^3$, preferably between 1.04 g/cm$^3$ and 1.05 g/cm$^3$.

However, it may also be of advantage if the material used for the base body 41 is a liquid-tight plastic and also contains optional additives and fillers, e.g. a thermosetting plastic, a transparent polystyrene or similar. The base body 31 should also have a gas permeability that will virtually prevent penetration by gases for a period of 48 or 72 hours. It has also been found to be of practical advantage if the total weight of the base body 41 and/or the separating mechanism 11 is variable, which will then enable the separating mechanism 11 and/or the base body 41 to be exactly modified to cater for different media 3, 4 in the mixture 2 to be separated. In order to achieve an exact physical separation process of the two media 3, 4 from the mixture 2 during the centrifugation process, the specific weight or the density of the material from which the base body 41 is made must be lower than the specific weight or density of one medium 3, 4 to be separated by the separating mechanism 11 on the one hand and higher than the lighter specific weight or density of one medium 3, 4 to be separated by the separating mechanism.

Depending on the different media 3, 4 or constituents to be separated from the mixture 2, it may be of advantage if at least part-regions or the entire internal surface of the interior 10 is provided with a coating 43, in order to assist the sliding motion of the separating mechanism 11 during the separation process and/or influence the mixture 2 by chemical and/or physical means or similar. When the base body 41 is inserted in the region of the open end face 19 of the container system 1, at least one surface disposed between the separating mechanism 11 and the oppositely lying end 7 may be provided with this coating 43, which may be of the type which detaches or dissolves from the surface on contact with the mixture 2 and can be used simultaneously as a means of fixing the separating mechanism 11, for example.

In the embodiment illustrated as an example here, the base body 41 of the separating mechanism 11 has at its centre and in the region of the longitudinal axis 15 a connecting orifice 44 between end regions 45, 46 spaced at a distance apart from one another in the direction of the longitudinal axis 15, and, as illustrated in the end region 45 shown here, a concave recess 47 may be provided, the shape of which may be more or less adapted to or match the part of the sealing device 21 facing it, for example the sealing stopper 22 of the closing device 9. This being the case, it is of advantage if, in its initial position, the recess 47 is moved into a position almost abutting with the sealing surface 34 of the sealing stopper 22, so that when the sealing stopper 22 is pierced by a cannula, not illustrated, a connection can be established between this cannula and the connecting orifice 44 in the base body 41. As also illustrated in a very simplified format, a separate insert part 48 is inserted or introduced into the connecting orifice 44, the design of the base body 41 and the insert part 48 being described in more detail with reference to other drawings below.

FIGS. 2 and 3 provide simplified diagrams on a larger scale showing one possible embodiment of the separating mechanism 11, which may be construed as an independent embodiment in it is own right, the same reference numbers being used as those used for FIG. 1.

In the direction of the longitudinal axis 15, the base body 41 has end regions 45, 46 spaced at a distance apart from one another, in effect being mutually spaced by a distance 49 or height. In the first or top end region 45 illustrated here, the base body 41 has an external dimension 51 in a plane 50 disposed perpendicular to the longitudinal axis 15 which is bigger than another external dimension 52 in the end region 46 in another plane 50a, parallel with the first plane 50 and also perpendicular to the longitudinal axis 15. Since the cross sections in the planes 16, 17 of the container receptacle 5 described above and the planes 50, 50a of the base body 41 are substantially circular in shape, the separating mechanism 11 can be readily inserted in the interior 10 of the container receptacle S irrespective of position. In the region of its abutment surface 42, the base body 41 is in the shape of a truncated cone with a cone angle 53 of between 0.1° and 3.0°, preferably between 0.6° and 0.8°. When the base body 41 is in the unclamped or non-deformed state, this cone angle 53 may match the taper of the interior 10 of the container between the two mutually spaced apart planes 16, 17.

It may be of advantage if the cone angle 53 of the base body 41 is slightly bigger than the taper of the interior 10 to prevent any jamming of the base body 41 in the area where the end region 46 merges into the abutment surface 42 on the inner surface of the container receptacle 5. By a judicious selection of the materials used for the container receptacle 5 and the separating mechanism 11, in particular the base body 41, the elasticity behaviour can be adapted accordingly and with it the pressure or friction force applied by the abutment surface 42 to the internal face of the container receptacle 5, thereby producing the associated sealing action.

The essential factor is that an internal periphery or an internal dimension 14 of the container receptacle 5 in the region of the first plane 16, 50 is the same as or smaller than an external periphery or an external dimension 51 of the base body 41 in its undeformed state in the same plane 16, 50. This means that, in its first end region 45, the external dimension 51 of the base body 41 in the undeformed state in the plane 50 perpendicular to the longitudinal axis 15 is the same as or bigger than the internal dimension 14 of the container receptacle 5 at its first open end 6 in the same plane 15.

FIG. 3 provides a plan view of the base body 41, which has a gap 54 extending between the two end regions 45, 56 and widens, in particular in a conical shape, starting from its centre or from the longitudinal axis 15 towards the abutment surface 42. As a result of the size or external dimension 51 selected for the base body 41 relative to the internal dimension 14 of the container receptacle 5 in the plane 16 illustrated in FIG. 1, as described above, in conjunction with the gap 54, it is very easy to mutually adjust these two components. With the same internal and external dimensions 14, 51, the abutment surface 42 can be seated in the region of the initial position and can be so with very light retaining forces between the abutment surface 42 and the internal face of the container receptacle 5.

If the external dimension 51 or the external periphery of the base body 41 in the non-deformed or non-clamped state is selected so as to be bigger than the internal dimension 14 in the initial position, a predefined retaining force can be obtained between the abutment surface 42 of the base body 41 and the internal face of the container receptacle 5 due to the elastic deformation of the base body 41 in co-operation with the gap 54. Selecting the clamping effect or differences in these dimensions also enables the displacement force created by the centrifugal effect, needed in the direction of the longitudinal axis 15 in order to produce a displacement or shift from the initial position into the operating position, to be fixed.

As also illustrated in FIG. 3, an arc length 55 of the gap 54 in the region of the abutment surface 42 in the container receptacle 5 and in the initial position illustrated in FIG. 1 is the same as the circumferential difference between the internal circumference of the container receptacle 5 in the plane 16 perpendicular to the longitudinal axis 15 in the region of the initial position and the internal circumference of the container receptacle 5 in the region of the operating position illustrated in FIG. 7, as will be described and illustrated below.

The gap 54 is bounded by gap faces 56, 57, between which a passage can be established for one of the two media to be separated—which is the lighter medium 3 in the embodiment illustrated as an example here—during the pre-definable displacement from the initial position into the operating position.

As may be seen from a comparison of FIGS. 2 and 3, the base body 41 has a connecting orifice 44 at its centre or in the region of the longitudinal axis 15, as briefly described above with reference to FIG. 1. This connecting orifice 44 enables the interior 10 of the container 4 to be filled via the base body 41 of the separating mechanism 11. In the section directed towards the first end region 45, this connecting orifice 44 has a clearance width 58 which is dimensioned to enable the interior 10 to be filled with an unobstructed flow of mixture 2. As also illustrated, starting from the first end region 45 of the clearance width 58, the connecting orifice 44 widens towards the other end region 46, specifically being of a truncated cone shape. As described above, the base body 41 has a concave recess 47 in its first end region 45, the shape of which matches the sealing surface 34 of the sealing stopper 22, and which is of a depth 59 in the region of the longitudinal axis 15, starting from the plane 50 and extending in the direction of the longitudinal axis 5. The diverging region of the connecting orifice 44 extends across a part-region of the distance 49, less the depth 59 between the two end regions 45 and 46 or planes 50 and 50a.

At the frustoconical diverging section of the connecting orifice 44 illustrated here, the insert part 48 is illustrated in a position in which it sits closer to the portion of the end region 46. When the container system is in the usage or normal position, the first end 6 is always higher than the other end 7 and because of the earth's attraction or gravitational force, the insert part 48 is always located or positioned in the area close to the end region 46.

In order to prevent the insert part 48 from moving out of the connecting orifice 44 towards the interior 10 of the container receptacle 5, a retaining mechanism 60, illustrated in a simplified format, is provided, which projects into the connecting orifice 44 at the end region 46. The embodiment illustrated here is only one of many possibilities and can be construed as an independent solution proposed by the invention in its own right. It retains the insert part 48 in this portion of the base body 41, restricting its ability to move in the direction of the longitudinal axis 15, and the retaining mechanism 60 is designed to permit a passage or flow irrespective of the position of the insert part 48 so that a flow can be established through the connecting orifice 44. In the embodiment illustrated as an example in FIG. 4, several webs 61—in this particular case three webs—are provided on the base body 41 and in particular are moulded onto it. In selecting the layout and design of the webs 61, allowance must be made for the gap 54 described above, to enable the two mutually facing gap faces 56, 57 to come into contact during the closing motion of the gap 54, as will be described in more detail below in connection with the operating position. Accordingly a flow passage is formed by the connecting orifice 44 and/or the gap 54, which can be respectively closed off as necessary and which can in fact be closed off by at least one automatically acting valve system.

This may be achieved by the insert part 48 moving into contact with the boundary walls of the connecting orifice 44 and/or as a result of the contact of the two gap faces 56, 57 with one another.

The external dimension of the insert part 48 is shown in simplified format by broken lines in FIG. 4, which provides a simple illustration of how a flow can be obtained between the external surface of the insert part 48 and the connecting orifice 44. As a result, a flow connection between the two spaced apart end regions 45, 46 of the base body 41 can also be obtained through the connecting orifice 44 when the insert part 48 sits in abutment with the retaining mechanism 60.

It is of advantage if the clearance width 58 (see FIG. 2) of the connecting orifice 44 in the first end region 45 in the plane 50 perpendicular to the longitudinal axis 15 is the same as or smaller than the external dimension of the insert part 48, in particular the part of the insert part 48 directed towards the end region 45, when the base body 41 and the separating mechanism 11 are in the initial position. This prevents the insert part 48 from moving through or out of the connecting orifice 44 and out of the base body 41.

In the embodiment illustrated as an example here, the insert part 48 is provided in the form of a truncated cone and is dimensioned so that when the base body 41 is in the non-deformed state and in the position in which the separating mechanism 11 is in the initial position prior to the start of the centrifugation process, a shifting movement is possible inside the connecting orifice 44 in the direction of the longitudinal axis 15 across a part-region of a length 62 (see FIG. 2).

Between the external abutment surface 42 and the connecting orifice 44, the base body 41 illustrated in FIGS. 2 and 3 has a substantially annular recess in the direction of the longitudinal axis 15, extending from the other end region 46 towards the first end region 45. This therefore forms a casing part 64 in the region of the external periphery of the base body 41. The layout and design of the recess 63 will depend on the material selected for the base body 41, the selected density and the resultant weight and can be freely selected depending on the intended application.

FIG. 5 illustrates another possible embodiment of the retaining mechanism 60 provided for the connecting orifice 44 of the base body 41, which may also be construed as an independent embodiment in its own right, the same reference numbers being used to denote the same parts described in FIGS. 1 to 4 described above.

In the embodiment illustrated as an example here, the connecting orifice 44 for receiving the insert part 48, which is not illustrated in this instance, may again be of a diverging frustoconical design over a part-region of the distance 49, starting from the end region 45 extending towards the other end region 46, as described in detail above with reference to FIGS. 2 to 4. The cross section of the connecting orifice 44 is designed to match the retaining mechanism 60 with a reduced cross section to form an orifice 65, a wall part 66 being formed between the orifice 65 and connecting orifice 44 in the end region 46 of the base body 41. Several webs or ribs 67 and grooves 68 may be provided on the wall part 66 facing the first end region and standing proud of and/or recessed in it. Accordingly, the orifice 65 is prevented from being totally completely closed off when the insert part 48 is in abutment with the wall part 66. As a result of this combination of ribs 67 and grooves 68, a higher flow volume can be achieved through the orifice 65 between the insert part 48 and the wall part 66. Similarly, however, it would also be possible to provide an alternating arrangement between the ribs 67 and grooves 68 around the periphery of the orifices 65 and the connecting orifice 44.

Figure 6:
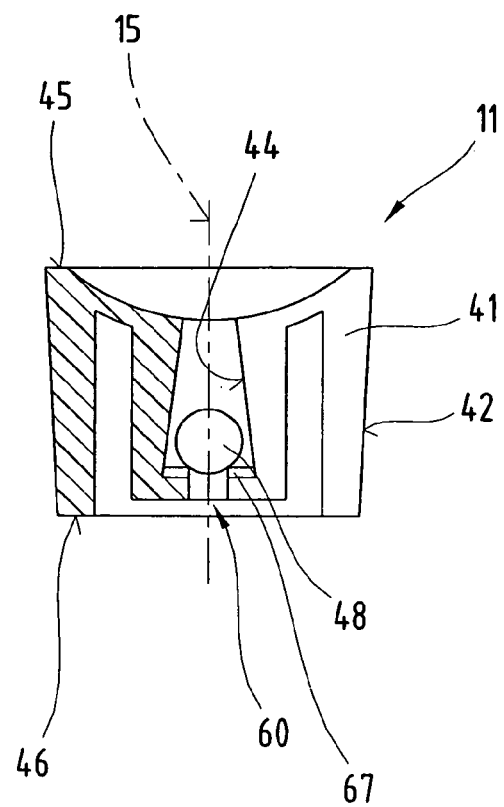
FIG. 6 is an enlarged diagram in section, showing a separating mechanism with a different insert part and retaining mechanism, seen from a side view.

FIG. 6 illustrates an embodiment of the base body 41 for obtaining a separating mechanism 11 that is similar to that already described in connection with FIGS. 2 to 4 but the insert part 48 in this case is of a different three-dimensional shape.

In the embodiment illustrated as an example here, the insert part 48 is in the shape of a ball and is illustrated in a position immediately adjacent to the end region 46. Here again, the retaining mechanism 60 must be provided in one of the embodiments described above in order to provide the flow connection between the two end regions 45, 46 through the connecting orifice 44. This may be achieved by providing several webs 61 and ribs 67 and/or recessed grooves 68 on the wall part 66.

FIGS. 7 and 8 illustrate the container system 1 with the separating mechanism 11 disposed in it and show the interior 10 filled with the mixture 2 described in connection with FIG. 1, which will be split or separated into the two media 3, 4 when subjected to centrifugal force, in particular during a centrifugation process. Accordingly, the lighter medium 3 is contained in the interior 10 between the separating mechanism 11 and the first end 6 and closing device 9 and the other heavier medium 4 is disposed in the container receptacle 5 between the separating mechanism 11 and the closed end 7.

As described above, the gap 54 (see FIG. 3) has the arc length 55 in the region of the abutment surface 42 in the first plane 16 between the gap faces 56, 57. Starting from the plane 16, the separating mechanism 11 moves towards the other end 7 and, because of the conical shape of the interior 10, the internal periphery constantly decreases so that after a displacement along a displacement path 69, the two gap faces 56, 57 forming the gap 54 are moved into contact with one another. Consequently, as the separating mechanism 11 is shifted or displaced from the initial position to the operating position illustrated in FIG. 7, the arc length 55 continuously decreases due to the constantly decreasing internal dimension 14 of the gap 54 (see FIG. 3), until the two gap faces 56, 57 are brought into a tight and preferably sealing abutment.

On establishing this mutual contact, the simple elastic displacement or reduction of the part length 55 of the gap 54 is completed so that an internal clearance dimension 70 and the internal periphery of the container receptacle 5 in the plane 71 perpendicular to the longitudinal axis in the region of the operating position corresponds to an external dimension 72 and periphery of the base body 41 when the gap 54 is in the closed position.

The pre-definable conical shape of the interior of the container receptacle 5 and the arc length 55 of the gap 54 in the base body 41, which can be selected beforehand, enable the exact displacement path 69 by which the separating mechanism 11 moves from the initial position into the operating position to be determined beforehand, guaranteeing a mechanical block and a locking or retaining fit inside the container receptacle 5. Since the displacement path 69 can be predetermined, it is possible to set the location and hence the associated position of the separating mechanism with respect to the operating position, irrespective of the filled quantity, without constituents of the mixture 2, in particular the medium 4, from getting into the space between the separating mechanism 11 and first end 6 or closing device 9. This displacement path 69 is approximately half the distance between the planes 16 and 17.

During the centrifugation process, the separating mechanism 11 migrates along the internal face of the container receptacle 5 in the direction of the longitudinal axis 15 towards the operating position, allowing the medium 3 to pass through the gap 54 into the space between the separating mechanism 11 and the closing device 9 and first end 6. Furthermore, the lighter medium 3 is also able to pass through the connecting orifice 44 because it is displaced into the region of the retaining mechanism 60 due to the centrifugal force acting on the insert part 48. It is of practical advantage if the density of the insert part 48 has a value which is lower than that of the heavier of the two media 3, 4 and higher than that of the lighter medium.

As an alternative, however, the density of the insert part 48 may be selected so that it is lower than the density of the lighter medium—which in this particular case is the medium 3—because the insert part 48 will float on this medium whatever the circumstances and will be moved into the connecting orifice 44 in the direction of the end region 45. Due to the complementary conical design, the connecting orifice 44 between the two spaced apart end regions 45, 46 is closed. This effect is enhanced by the fact that because the gap 54 narrows until the two gap faces 56, 57 are in contact with one another, the cross section of the connecting orifice 44 is slightly reduced, thereby producing an additional clamping force between the base body 41 and the insert part 48 in the section of the mutual abutment surfaces. Consequently, the insert part 48 sits against the boundary walls of the diverging section of the connecting orifice 44 in a sealing and in particular liquid-tight fit in the operating position.

It may be preferable to select a liquid-tight, in particular water-tight and possibly also gas-tight, plastic as the material or substance for the insert part 48, for example selected from the group consisting of polyethylene terephthalate (PET), polypropylene (PP), polyethylene (PE), high density polyethylene (PE-HD), acrylonitrile butadiene styrene copolymers (ABS), polystyrene (PS) or similar or a combination of these. A whole range of additives could also be added to the material, for example in order to make an adjustment to obtain the exact, predefinable density. This being the case, the density should be between 1.02 g/cm$^3$ and 1.07 g/cm$^3$, preferably between 1.04 g/cm$^3$ and 1.05 g/cm$^3$. It is also of advantage if the density of the insert part 48 is selected so that it is slightly higher than the density of the base body 41, because this will mean that a flow can continue through the connecting orifice 44 between the two interiors of the container receptacle 5 separated by the separating mechanism until shortly before the operating position is reached.

It has also proved to be of advantage if at least certain regions of the base body 41 and/or the insert part 48 are provided with a coating, such as a layer of silicone for example, because this will ensure that no blood cells are able to adhere to them during the centrifugation process leading to contamination of the medium 3 separated off into the area between the closing device 9 and separating mechanism 11.

The container system 1 may be assembled in the following manner.

The separating mechanism 11 is inserted through the open end of the prepared container receptacle 5, after which the interior 10 of the container receptacle 5 is brought to a pressure below atmospheric pressure, and indeed the entire area around the container is evacuated or reduced to this vacuum pressure, and the closing device 9 is then inserted in the open end of the container receptacle 5 in order to seal it and maintain the vacuum pressure. Due to the gap 54 in the base body 41 described above, once the latter has been inserted in the interior 10, it can also be evacuated to the desired vacuum pressure and the closing device only then fitted or inserted on the open end face 19 of the container receptacle 5 in order to obtain a seal and maintain the vacuum pressure.

FIGS. 9 to 13 illustrate another possible embodiment of the container system 1, which may also be construed as an independent embodiment of the invention in its own right, with the separating mechanism 11 inserted, the same parts being denoted by the same reference numbers as those in respect of the preceding FIGS. 1 to 8. To avoid unnecessary repetition, reference should be made to the detailed description relating to FIGS. 1 to 8 for an explanation of the design of and choice of materials, in particular for the container receptacle 5, the separating mechanism 11 and the closing device 9.

The container receptacle 5 in the embodiment illustrated as an example here has the first end 6, which is open in this instance, and the other end 7 spaced at a distance apart from it in the direction of the longitudinal axis 15. The container wall 12 bounds the interior 10 and forms an internal face 73 directed towards it. As may also be seen, the internal dimension 14 in the region of the first plane 16 directed towards the first end 6 of the container receptacle 5 is virtually the same as or identical to the internal dimension 18 in the region of the other schematically indicated plane 17 in the in the region of the end 7. Since the two internal dimensions 14, 18 are the same, the internal face matches a cylindrical wall surface of the container wall 12 between the two planes 16, 17.

The base body 41 of the separating mechanism 11 has the two end regions 45, 46 spaced at a distance apart from one another in the direction of the longitudinal axis 15. At its external periphery, the base body 41 is bounded by an external face 74 between the two end regions 45, 46 and this external face 74 may correspond more or less to the internal dimensions 14 and 18 of the cylindrical container. If the dimensions of the base body 41 are selected so that the external face 74 moves into abutment against the internal face 73 of the container receptacle 5, the entire external face 74 forms a sealing device 75 between the latter and the internal face 73 in the mutually abutting region.

It is also possible to select an external dimension or diameter for the external face 74 that is bigger than the internal dimension 14 and 18, in which case, if an appropriate material is selected for the base body 41, the external face 74 will sit with sufficient pressing force against the internal surface 73, producing a seal between the two components.

As an alternative, however, it would also be possible to provide the sealing device 75 in the form of at least one peripheral sealing lip 76 standing proud of the external face 74 of the base body 41, in which case this sealing lip 76 may be provided in one of the two end regions 45, 46. Accordingly, an external dimension of the external face 74 will be smaller than the internal dimensions 14, 18 of the container receptacle 5 and only the sealing lip 76 will sit in abutment on the internal surface 73. In order to improve the closing action and obtain a more accurate positional guidance of the base body 41 during the displacement from the initial position into the operating position, it may be of advantage if the sealing device 75 is provided in the form of several sealing lips 76 projecting out from the external face 74, which will preferably be arranged in an end region 45, 46 of the base body 41. This means that a continuous sealing lip 76 will be provided around at least each of the end regions 45, 46.

Naturally, however, it would also be possible to provide several of these sealing lips 76 between the two end regions 45, 46, thereby providing a flap-type sealing arrangement. The displacement force which must be applied by the centrifugal force acting on the base body in order to achieve the displacement described above can be fixed depending on the number and design of the sealing lips 76.

The connecting orifice 44 providing the flow passage between the two end regions 45, 46 is disposed inside the base body 41 in the region of the longitudinal axis 15. Accordingly, starting from the other end region 46 and extending towards the first end region 45 in a plane perpendicular to the longitudinal axis, the connecting orifice 44 has an internal dimension 77, which is at least the same as or smaller than an external dimension 78 of a support body 79 of the insert part 48 to be inserted in the connecting orifice 44.

FIGS. 10 to 12 illustrate the individual parts making up the separating mechanism 11 on a larger scale, with the separating mechanism 11 in the initial position inside the container receptacle 5, so that the insert part 48, in particular the support body 79, projects through the connecting orifice 44, at least in certain regions, but the insert position is disposed between the base body 41 and the first or open end 6 of the container receptacle 5 in the initial position. Consequently, the interior 10 can be filled by means of the sealing stopper 22 of the sealing device 21, which is pierced by a hollow needle or cannula, for example.

To enable the mixture 2 to pass from the interior and into the region of the insert part 48 and the base body 41, several catch elements 80 of a retaining mechanism 81 are provided on the base body 41 in the first end region 45, distributed around certain regions of the periphery of the connecting orifice 44, between which the mixture 2 is able to pass into the connecting orifice 44 in certain regions and then flow on into the interior 10. These individual catch elements 80 are designed so that when a shoulder 82 projecting out from a support body 79 of the insert part 48 sits against the catch elements 80, an abutment surface 83 of the insert part 48 is set back at a distance from a sealing surface 84 of the connecting orifice 44, thereby providing a flow connection between the two end regions 45, 46 via the connecting orifice 44. The shoulder 82 therefore co-operates with the individual catch elements 80 of the retaining mechanism 81 and positions the insert part 48 relative to the base body 41 in the position described above, in which a flow is able to pass between the support body 79 partially projecting into the connecting orifice 44 and the sealing surface 84 of the connecting orifice 44.

This position in which the interior 10 is filled is illustrated in FIG. 9, which also provides a simplified illustration of the interior already filled with the mixture 2 consisting of the two different media 3, 4. Accordingly, the retaining mechanism 81 is disposed on the base body 41 on the side directed towards the first end 6 of the container receptacle 5. The individual catch elements 80—four such catch elements 80 being provided in the embodiment illustrated as an example here—form an envelope 85 at the end directed towards the longitudinal axis 15, which has a clearance width 86 in a plane perpendicular to the longitudinal axis 15, which is shorter than an external dimension 87 of the shoulder 82 of the insert part 48 projecting out from the support body 79. Consequently, a joining surface 88 of the shoulder sits in abutment with at least certain regions of the nose-shaped catch elements 80.

A groove-shaped recess 89 is also provided in the region of the connecting orifice 44 in the base body 41, the width 90 of which in the direction of the longitudinal axis 15 corresponds to at least a thickness 91 of the shoulder of the insert part 48 to be inserted in this recess 89 in the same direction.

This sealing position of the insert part 48 in the base body 41 is illustrated in FIG. 13, which shows the shoulder 82 having moved beyond the individual catch elements 80 during the centrifugation process so that the support body 79 of the insert part 48 is disposed in a sealing and in particular fluid-tight position in the connecting orifice 44. Accordingly, the abutment surface 83 of the support body 79 co-operates with the sealing surface 84 of the connecting orifice 44, as a result of which the flow passage between the two end regions 45, 46 is closed when the centrifugation process is terminated. As a result of the differences in dimensions described above, in particular the diameter between the clearance width 86 of the envelope 85 and the external dimension 87 of the shoulder 82, the catch elements 80 engage at least in certain regions behind the shoulder 82, which additionally helps to fix the insert part 48 in its sealing position inside the connecting orifice 44. The groove-shaped recess 89 at the side directed towards the first end region 45 and first end 6 of the container receptacle 5 is bounded in at least certain regions by the catch elements 80 of the retaining mechanism 81. The advantage of this is that, starting from the operating position in which a flow connection is possible between the two end regions 45, 46 via the connecting orifice 44, only a short displacement path is necessary between the two parts, namely the insert part 48 and the base body 41, in the direction of the longitudinal axis 15 in order to provide a sealed closure in the region of the separating mechanism 11 between the two media 3, 4 separated from one another on the one hand, and, on the other hand, to ensure that there is an unobstructed flow through the connecting orifice 44 in the initial position until the operating position is established.

To facilitate this relative displacement, it is of advantage if the catch elements 80 on the side remote from the groove-shaped recess 89 are of a conical or oblique shape, diverging from the region of the longitudinal axis 15 towards the external face 74. As a result of these catch elements, a funnel-shaped seating orifice is formed, tapering from the end region 45 in the direction of the other end region 46 to the connecting orifice 44, as a result of which the force to be applied to permit a flow between the insert part 48 and the base body 41 can be fixed, depending on how steep the angle is, and hence the instant at which the relative displacement of the insert part 48 into the sealing position in side the base body 41 takes place during the course of the centrifugation process.

At the end remote from the shoulder 82, the insert part 48 also has a comically tapering shoulder part 92 adjoining the support body 79, the purpose of which is to facilitate the relative displacement between the insert part 48 and the base body 41 into the sealing position. This arrangement likewise facilitates the process of inserting and positioning the insert part 48 in its initial position in the base body 41 prior to the start of the centrifugation process because positioning is assisted by the surfaces of the shoulder part 92 and the catch elements 80, which are respectively inclined at an angle to the longitudinal axis 15.

In order to provide additional sealing between the insert part 48 and the base body 41 in the region of the connecting orifice 44, another option, illustrated by broken lines in FIG. 10, is to provide a stop ring 93 co-operating with and complementing the conically tapering shoulder part 92 of the insert part 48, in the region of the connecting orifice 44. As a result of the complementary design of the surfaces of the conically shaped insert part 92 and stop ring 93 angled relative to the longitudinal axis 15, the flow passage 44 between the two end regions 45, 46 can also be sealed in this region. This being the case, this seal may be provided in addition to the seal between the abutment surface 83 and sealing surface 84 or a seal is provided exclusively between the shoulder part 91 and stop ring 93. When the separating mechanism 11 is in the operating position, the conically tapering shoulder part 92 of the insert part 48 provides a seal and in particular a fluid-tight seal on the stop ring 93.

Another option of ensuring that the filling process runs correctly is to provide a raised part 94 on the shoulder 82 on the side of the shoulder 82 remote from the support body 79, indicated by broken lines in FIG. 12, extending downwards from the longitudinal axis 15 towards the peripheral regions of the shoulder 82, so that the mixture 2 is able to run along the surfaces, which are inclined relative to the longitudinal axis 15, and then flow through the connecting orifice 44 into the interior 10. The filling process is also made easier as a result of the vacuum prevailing in the interior, placing the interior at a pressure below atmospheric pressure and resulting in a suction process, which means that the degree to which the container is filled can be fixed by an appropriate selection of the vacuum pressure.

At the end of the filling process, the entire separating mechanism 11 is in its initial position described above, in other words close to the open end of the container receptacle 5 and close to the closing device 9. The mixture 2 of the two media 3, 4 to be separated from one another is disposed between the separating mechanism 11 and the end 7 of the container receptacle 5, which is closed in this instance. As a result of the density selected for the base body 41 and the insert part 41, a relative displacement of the base body 41 is effected along the internal face 73 of the container receptacle 5 towards the end 7 at the start of the centrifugation process. The density of the base body 41 is between 1.04 g/cm$^3$ and 1.05 g/cm$^3$ and that of the insert part 48 is between 1.06 g/cm$^3$ and 1.07 g/cm$^3$. Once a certain displacement path has been overcome, the end region 46 of the base body 41 reaches the top end of the mixture 2 and, because of the active centrifugal forces, the media 3, 4 already start to separate due to the different density values. The mixture, which might be full blood for example, has a density of between 1.05 g/cm$^3$ and 1.06 g/cm$^3$. The density of the serum or plasma is between 1.02 g/cm$^3$ and 1.03 g/cm$^3$ and that of the blood cells is approximately 1.08 g/cm$^3$.

The lighter medium 3, denoted by reference 3 in this example, remains at the side of the container receptacle 5 directed towards the end 6, and the heavier medium 4, denoted by crosses, is moved towards the end 7, which is closed in this example. The base body 41 is moved in the direction towards the other end 7 of the container receptacle 5 due to the centrifugal force acting on it and the possibility explained above whereby the lighter medium 3 is able to pass through the connecting orifice 44 to the side of the base body 41 directed towards the closing device 9. This continues until the end region 46 of the base body 41 comes into to contact with the boundary surface between the heavier and the lighter medium 4, 3 due to the differences in density specified above and the relative displacement between the base body 41 and the container receptacle 5 terminates. Another relative displacement then takes place, whereby the insert part 48 is shifted relative to the base body 41 into the sealing position inside the base body 41, ensuring that there can be no further passage or mixing between the now separated media 3, 4. To facilitate this displacement without having to force one of the two media 3, 4, a recess 95 is provided inside the insert part 48 in the region of the shoulder part 92 and support body 79, indicated by broken lines in FIG. 12, which holds the medium 3 and/or 4 so that the shoulder 82 can be displaced beyond the catch elements 80 into the groove-shaped recess 89 provided in the region of the connecting orifice 44.

Consequently, a sealed position is obtained both in the region between the internal face 73 of the container receptacle 5 and the external face, as well as between the sealing lips 7, the base body 41 and between the base body 41 and the insert part 48.

Figure 15:
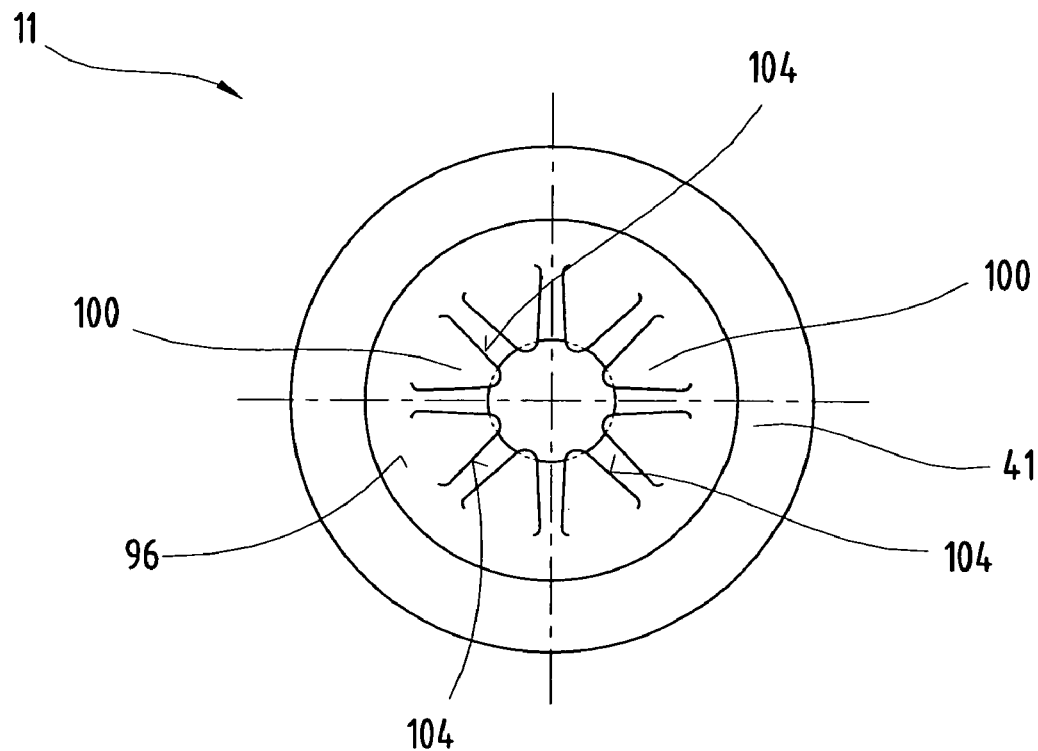
FIG. 15 is a plan view of the base body of the separating mechanism illustrated in FIG. 14 and with the insert part removed.
Figure 16:
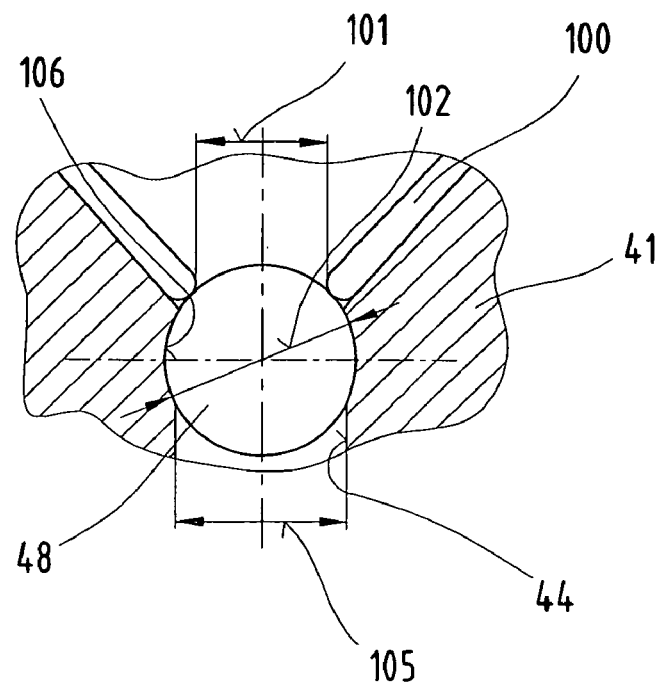
FIG. 16 is a simplified, schematic diagram in section, showing a side view of a part-region of the separating mechanism illustrated in FIGS. 14 and 15 in its operating position.

FIGS. 14 to 16 illustrate another embodiment of the separating mechanism 11 inside the container receptacle 5, which may also be construed as an independent solution proposed by the invention in its own right, the same parts again being denoted by the same reference numbers as those used for the description of FIGS. 1 to 13. To avoid unnecessary repetition, particularly with regard to the design of the container receptacle 5, its closing device 9 and the individual embodiments of the separating mechanism 11, reference should be made to the description of FIGS. 1 to 13 above.

The container receptacle 5 with the container wall 12 bounding the interior 10 is again of a cylindrical design in the region of its internal surface 73 between the spaced apart ends 6, 7, as described above in connection with FIGS. 9 to 13. Accordingly, the interior 10 is of the same dimensions 14, 18 between the two ends 6, 7 (see FIG. 9).

The base body 41 is again provided with the sealing device 75 between the base body 41 and the internal surface 73 of the container receptacle 5, which preferably extends around it continuously, reliably preventing a passage for the media 3, 4 making up the mixture 2 between the base body 41 and the container wall 12 (see FIG. 9). The sealing device may again be provided in the form of at least one peripheral sealing lip 76 standing out from the base body 41 and may be made from the same material as the base body 41 or a different material. If the sealing lip 76 is made from a different material from the base body 41, it may be retained on it, moulded on it or made as an integral part of it. Any system known from the prior art may be used.

Another option, however, is to make the base body 41 and the sealing lip 76 from the same material but with different densities or elasticity values, in which case the sealing lip 76 will be specifically designed to produce a reliable separation between the two media 3, 4 once the separating process is complete.

The base body 41 illustrated here, particularly in the left-hand part of FIG. 14, may be of the same three-dimensional shape as that illustrated in FIG. 10 in the region directed towards the internal surface 73, as indicated by broken lines. The base body 41 of the separating mechanism 11 in this embodiment has a conical recess 96 tapering out from the peripheral regions in the direction of the longitudinal axis 15 starting from the first end region 45 to its other end region 46, and opens into the connecting orifice 44 in the region of the longitudinal axis 15. It is of particular advantage if the base body 41 is of a funnel-shaped design starting from the first end region 45 as far as its other end region 46, in particular in the direction of the longitudinal axis 15, which will enable a considerable saving in the amount of material needed for the base body 41. With the funnel-shaped design, the base body 41 has more or less a same wall thickness 97 and can be made by a simple injection moulding process, for example.

As described above, the recess 96 tapers in a conical arrangement and its three-dimensional shape is fixed by a boundary surface 98. When the separating mechanism 11 is in the initial position, the insert part 48 is again disposed between the base body 41, in particular the recess 96, and the sealing stopper 22 of the closing device 9. In the embodiment illustrated as an example here, the insert part 48 is provided in the form of a ball, which is maintained in position relative to the base body 41 by a retaining mechanism 99 in the initial position, so that a flow of the mixture 2 with which the interior 10 is to be filled is always able to pass from the first end 6, which may be closed as necessary, into the interior 10 through the separating mechanism 11.

This retaining mechanism 99 is disposed in a transition region between the connecting orifice 44 and the conically tapering recess 96 on the base body 41. Starting from the connecting orifice 44 and longitudinal mid-axis 15, the recess 96 diverges in a conical arrangement towards the external face 74 and the end region 45. The retaining mechanism 99 is provided in the form of several projecting catch elements 100 or ribs distributed around the periphery of the connecting orifice 44 and projecting into it from the external face 74 towards the longitudinal axis 15. At their end regions directed towards the longitudinal axis 15, these catch elements form an envelope in a plane perpendicular too the longitudinal axis 15 with a clearance width 101, which is shorter than an external dimension 102, in particular a diameter of the ball-shaped insert part 48.

As may also be seen from the diagrams given in FIGS. 14 and 15, the individual catch elements 100 in the transition region between the boundary surface 98 of the conical recess 96 and the connecting orifice 44 stand proud of this boundary surface 98. As a result of the plurality of catch elements 100 provided around the periphery of the connecting orifice 44 and the projection 103, which also decreases starting from the connecting orifice 44 in the direction towards the first end region 45 of the base body 41 relative to the boundary surface 98, flow passages 104 are formed between the individual catch elements 100.

These flow passages 104 ensure a reliable flow of the mixture 2 with which the interior 10 is being filled, even when the insert part is abutting against the catch elements 100. This continues until the insert part 48 has been displaced from its initial position into the operating position and the sealing operating position illustrated in FIG. 16. In the initial position, the insert part 48 is supported against the side of the catch elements 100 remote from the connecting orifice 44. The external dimension, in particular the diameter, of the ball-shaped insert part 48 is selected so as to be bigger than a diameter 105 of the connecting orifice 44 in the embodiment illustrated as an example here.

As may be seen most clearly from FIG. 14, in order to accommodate and support the insert part 48 in the base body 41, in particular in the sealing position, a bearing surface 106 designed to match the ball-shaped insert part 48 is provided in the transition region between the connecting orifice 44 and the retaining mechanism 99 and boundary surface 98 of the conically tapering recess 96. The purpose of this bearing surface 106 is to provide a sealing closure between the media 3, 4 separated from one another on completion of the centrifugation process in co-operation with the ball-shaped insert part 48, and the catch elements 100 of the retaining mechanism 99. The bearing surface 106 therefore acts as a sealing surface between the external face of the insert part 48 and the base body 41.

The differences in dimensions specified above, in particular the clearance width 101 of the enveloping circle or envelope of catch elements 100 and the external dimension 102 of the spherically shaped insert part 48, fix the position of the insert part 48 relative to the base body 41 once the insert part 48 has passed through the retaining mechanism 99, whilst the insert part 48 can also be additionally applied by the individual catch elements 100 against the bearing surface 106 with a specifically directed contact force.

As also illustrated, at the other end region 46 immediately adjacent to the connecting orifice 44, the base body 41 is provided with several guide elements 107 extending on the side remote from the longitudinal axis 15 and in a plane perpendicular to the longitudinal axis 15, and an outer envelope formed by the ends of the guide elements 107 more or less corresponds to an external dimension of the base body 41 at its first end region 45. This design and layout of the guide elements 107 is intended to fix the base body 41, which is also funnel-shaped, in its position relative to the container receptacle, which will prevent any tipping during the displacement thereby ensuring that the seal is not broken in the region of the sealing lips 76. These guide elements 107 may be of any three-dimensional shape, an arcuately curving contour being of particular advantage in order to generate a certain degree of springing or biassing action starting from these guide elements 107 towards the internal surface 73 of the container receptacle 5.

Naturally, however, it would also be possible, in the non-biassed state, for the dimension of the external envelope to be bigger than the external dimension of the base body 41 and the internal dimension 14, 18 of the interior 10. To ensure that the base body 41 is securely prevented from tipping, it is of advantage if the guide elements 107 stand proud at the side remote from the first end region 45 in the direction of the longitudinal axis 15 by means of a projection 108, which essentially corresponds to a height 109 of the base body 41 in the same direction.

Figure 17:
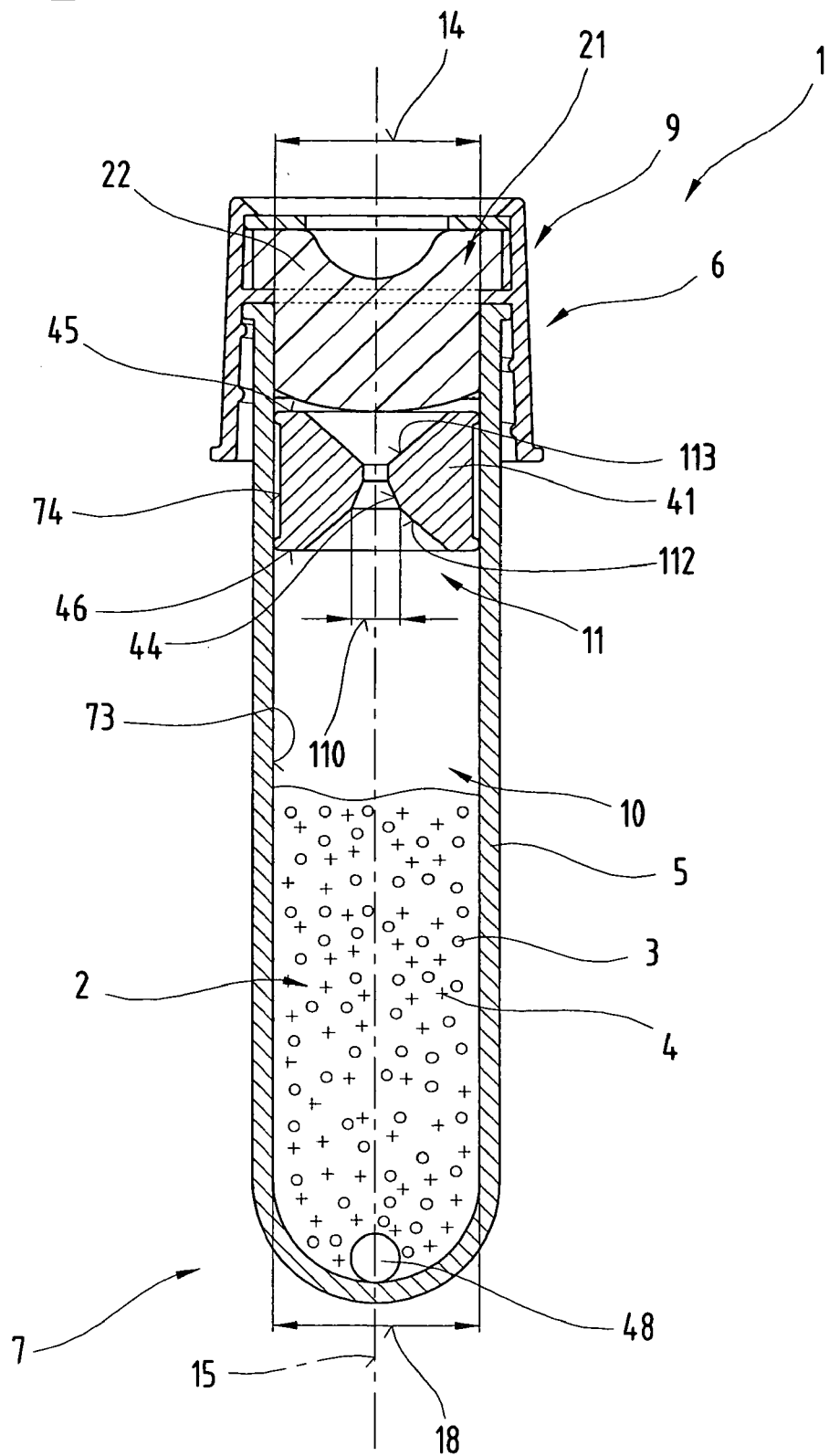
FIG. 17 is a simplified, schematic diagram in section, showing a side view of another embodiment of the container system proposed by the invention with a different separating mechanism disposed in the initial position and a sealing device.
Figure 18:
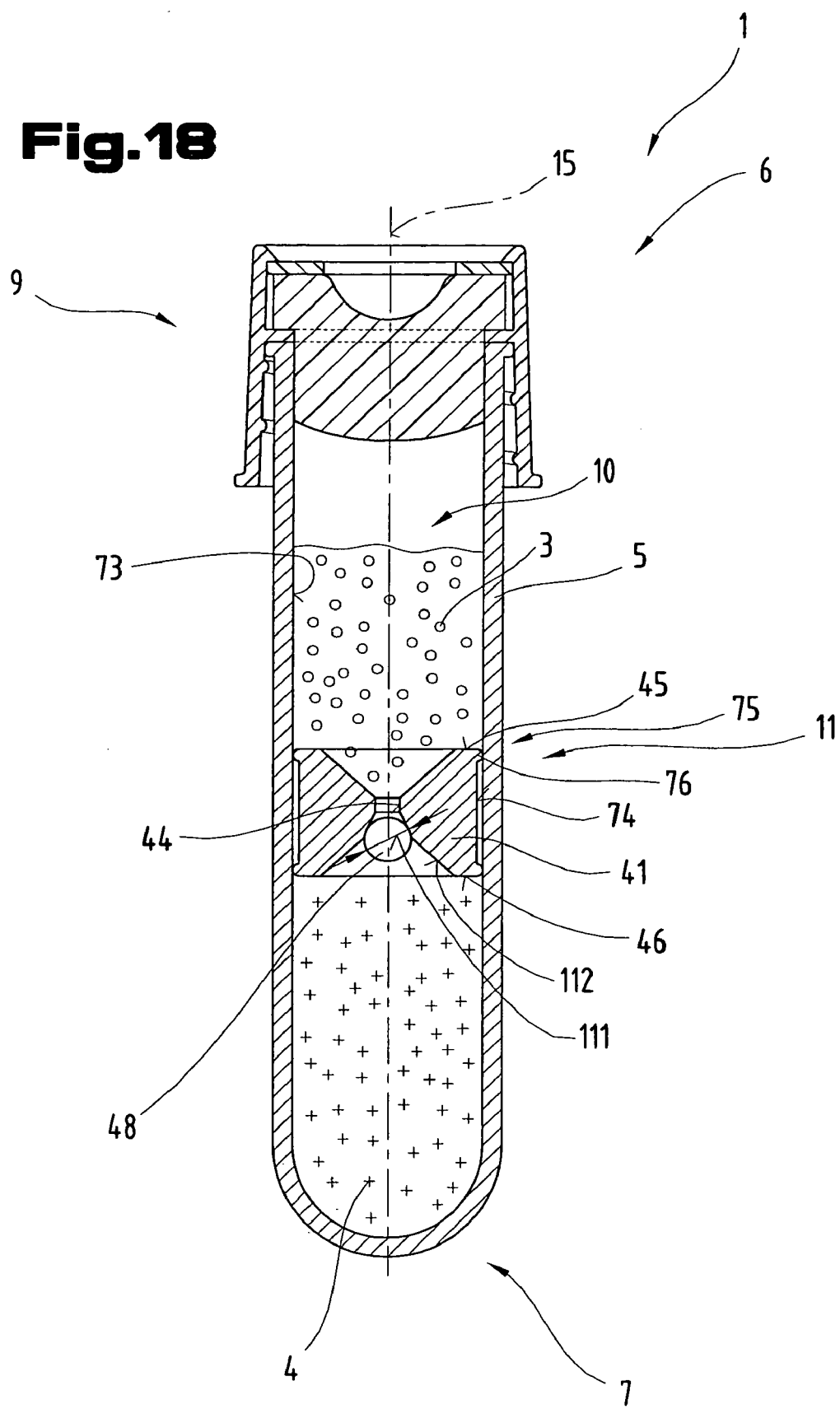
FIG. 18 is a simplified, schematic diagram in section, showing a side view of the container system illustrated in FIG. 17 in its operating position.

FIGS. 17 and 18 illustrate another embodiment of the separating mechanism 11 inside the container receptacle 5, which may also be construed as an independent embodiment, the same parts being shown by the same reference numbers as those used for FIGS. 1 to 16 above. The design of the container receptacle 5, its closing device 9 with the sealing device 21, in particular its sealing stopper 22, may be taken from the description of the embodiments illustrated in FIGS. 1 to 16. Reference should therefore be made to these drawings in order to avoid unnecessary repetition.

The container receptacle 5 bounds the interior 10 and has the ends 6, 7 spaced at a distance apart from one another in the direction of the longitudinal axis 15, at least one of which has an orifice. The separating mechanism 11 is again inserted in the interior 10 and consists of the base body 41 with the flow passage inside it, which can be closed off as necessary. The base body 41 has the end regions 45, 46 spaced apart from one another in the direction of the longitudinal axis 15, between which the external face 74 bounding the base body 41 extends. At least one sealing device 765 with at least one sealing lip 76 extending around the base body 41 is provided between the base body 41 and the internal surface 763 of the container receptacle 5. The sealing device 75 may be provided with at least one but preferably several sealing lips 76 and may be of the design described with reference to FIGS. 9 to 13.

FIG. 17 illustrates the container system 1 with the separating mechanism 11 in the initial position and the mixture 2 of media 3, 4, in which case the base body 41 is again close to the closing device 9. When subjected to centrifugal force, the base body 41 can be displaced towards the other end 7 into its operating position with the insert part 48 illustrated in FIG. 18.

In addition to the base body 41, the separating mechanism 11 in this example of an embodiment has at least one insert part 48, which is disposed in the interior of the container receptacle 5 when the separating mechanism 11 is in the initial position between the base body 41 and the other end 7, which in this particular instance is closed. The flow passage is provided by the round connecting orifice 44 in the base body 41, preferably in the form of a bore, with an internal orifice width 110 which decreases at least in certain regions in the direction of the longitudinal axis 15 from the other end region 46 through to the first end region 45, and an external dimension 111 of the insert part 48 in a plane perpendicular to the longitudinal axis 15 is bigger than the smallest internal orifice width 110 of the connecting orifice 44 so that the insert part 48 produces a secure seal in the region of the connecting orifice 44.

As a result of the decreasing orifice width 110 described above, this section of the connecting orifice 44 tapers in a conical arrangement, in which case it is of advantage to select the biggest internal orifice width 110 so that it is bigger than the external dimension 111 of the insert part 48. This enables the insert part 48 to enter the connecting orifice 44 at or shortly after the start of the centrifugation process, and the extent of the reduction in the internal orifice width 110 will determine the conical angle of the connecting orifice 44. A self-inhibiting clamping action of the insert part 48 in this section of the connecting orifice 44 will be guaranteed, depending on the steepness of the angle.

The key aspect of this embodiment is the fact that the base body 41 has a density of between 1.06 g/cm$^3$ and 1.07 g/cm$^3$ and the insert part 48 has a density of between 1.04 g/cm$^3$ and 1.05 g/cm$^3$. This ensures that, because of the progressive separation of the two media 3, 4 from the mixture 2 and due to the density values of the two media 3, 4 specified above, the base body is able to sink through the lighter medium 3 until it reaches the boundary surface between the two media 3, 4. As a result of the density selected for it, the insert part floats on the unseparated mixture 2 or is kept hovering within the mixture 2, so that when the two media 3, 4 start to separate, the lighter constituent floats above the heavy blood cells and the insert part 48, which has a lower density than the serum or plasma, and rises as far as the boundary surface between the two media 3, 4.

When subjected to centrifugal force, the base body 41 is moved from its initial position in the direction of the longitudinal axis 15 towards the end 7, which is closed in this particular instance, so that the lighter medium, in this case the medium denoted by reference 3, is able to pass through the connecting orifice 44, which is not yet closed, into the interior 10 of the container system 1 disposed between the base body 41 and the closing device 9, after which the connecting orifice 44 is closed off by the insert part 48 in the manner described above when the base body 41 makes contact in the region of the boundary surface between the two media 3, 4. As a result of its higher density, the base body 41 sinks deeper into the medium 4, as a result of which the insert part 48 is securely held in a sealing and in particular liquid-tight position in the connecting orifice 44 on completion of the centrifugation process, maintained in a type of clamped seating.

This being the case, it is of advantage to provide the insert part 48 in the form of a ball. To ensure that the insert part 48 assumes its position correctly at or shortly after the end of the centrifugation process, it is of advantage if the base body 41 of the separating mechanism 11 has a conical recess 112 tapering from the other end region 46 to the first end region 45, which opens into the connecting orifice 44 in the region of the longitudinal mid-axis 15. This recess 112 extends across a part-length of the base body 31 in the direction of the longitudinal axis 15.

For the filling process, it is of advantage if the base body 41 of the separating mechanism 11 has another conical recess 113 tapering from the first end region 45 towards the other end region 46, which also opens into the connecting orifice in the region of the longitudinal axis 15 and also extends across a part-length of the base body 41 in the direction of the longitudinal axis 15.

In the embodiments illustrated in FIGS. 9 to 18, the internal dimensions 14, 18 of the container receptacle 5 in the region of its internal surface 73 are always more or less identical, so that the interior 10 is bounded by a quite exact cylinder wall.

Figure 19:
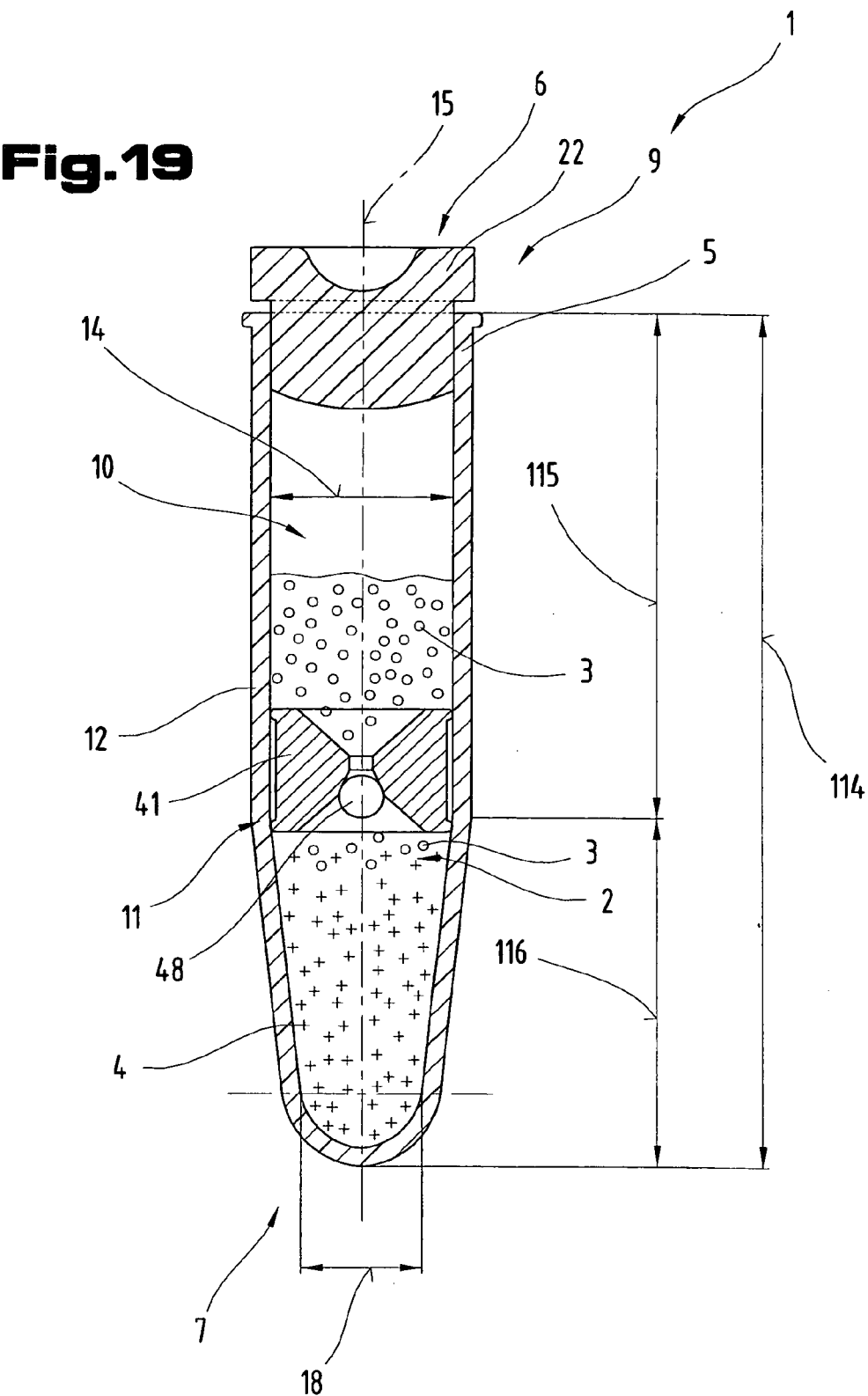
FIG. 19 is a simplified, schematic diagram in section, showing a side view of a different embodiment of the container system proposed by the invention with a separating mechanism disposed in its operating position.

FIG. 19 illustrates another option for an embodiment of a container receptacle 5, the same parts being denoted by the same reference numbers as those used for FIGS. 1 to 18 above. Only a part of the closing device 9 is illustrated, namely the sealing stopper 22.

In the direction of its longitudinal axis 15, the container receptacle 5 has a total length 114, which has the same internal dimension 14 across a first part-length 115 starting from the end 6, which in this instance is open, and extending towards the other closed end 7 in a plane perpendicular to the longitudinal axis 15, this portion therefore being cylindrical. Another part-length 116 of the container receptacle 5 adjoining the first part length 115 has a decreasing internal dimension 18 starting from the internal dimension 14, which is smaller than the first dimension 14 in the region of the other end 7.

Selecting the individual part-length 115, 116 as a ratio of the total length 114 provides a simple means of fixing a pre-definable position of the separating mechanism 11 inside the container receptacle 5 after the centrifugation process, in which the separating mechanism 11 is fixed in its position relative to the container receptacle 5. The selection of the part-lengths 115, 116 will depend on the total full volume of the mixture 2 in the interior 10, guaranteeing a reliable separation between the two separated media 3, 4 in the interior 10, without any subsequent mixing being possible once the centrifugation process is finished whatever the circumstances. It is irrelevant whether a part-quantity of the light medium 3 is left in the interior 10 between the separating mechanism 11 and the closed end 7 of the container receptacle 5. This is schematically illustrated by a few bits of the medium 3 in this section of the container 5. The design of the separating mechanism 11 used with this container receptacle 5 may be the same as that described with reference to FIGS. 1 to 18.

The quantities of the mixture 2 and its constituent elements—media 3, 4—illustrated in the drawings are given purely by way of example and neither the total quantity nor the individual quantities necessarily correspond to the actual quantities.

Figure 20:
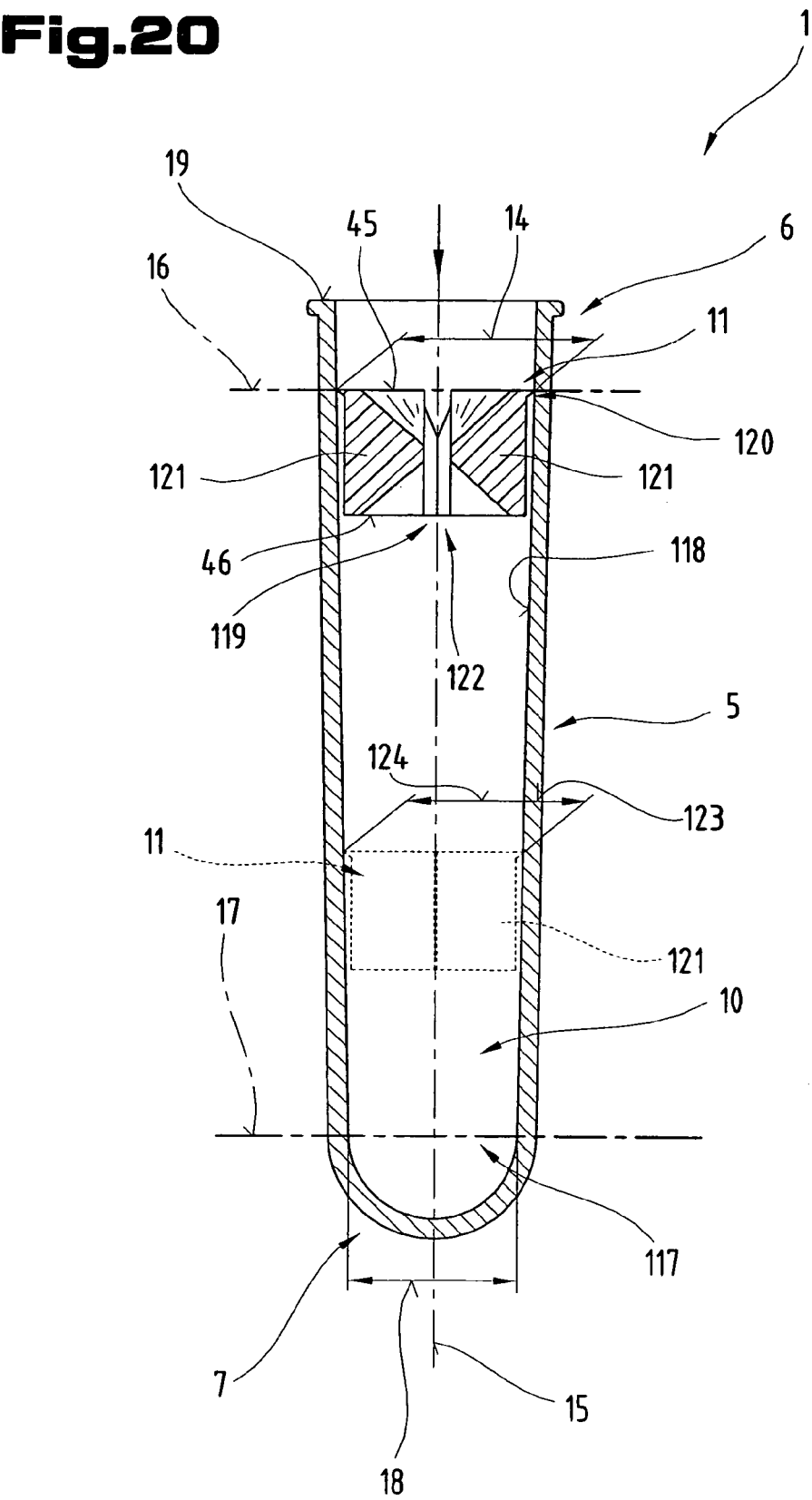
FIG. 20 is a simplified, schematic diagram in section, showing a side view of another embodiment of the container system proposed by the invention with a different separating mechanism disposed in its initial position, with the sealing device removed.
Figure 21:
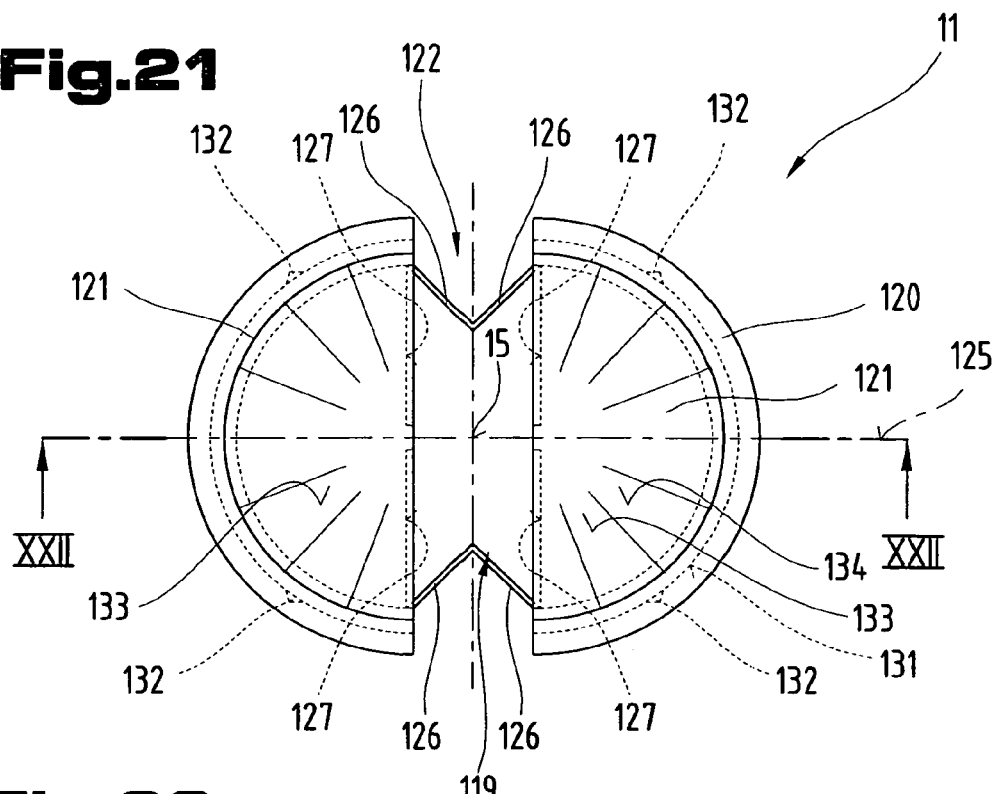
FIG. 21 is a simplified, schematic diagram on an enlarged scale, showing a plan view of the separating mechanism illustrated in FIG. 20.
Figure 22:
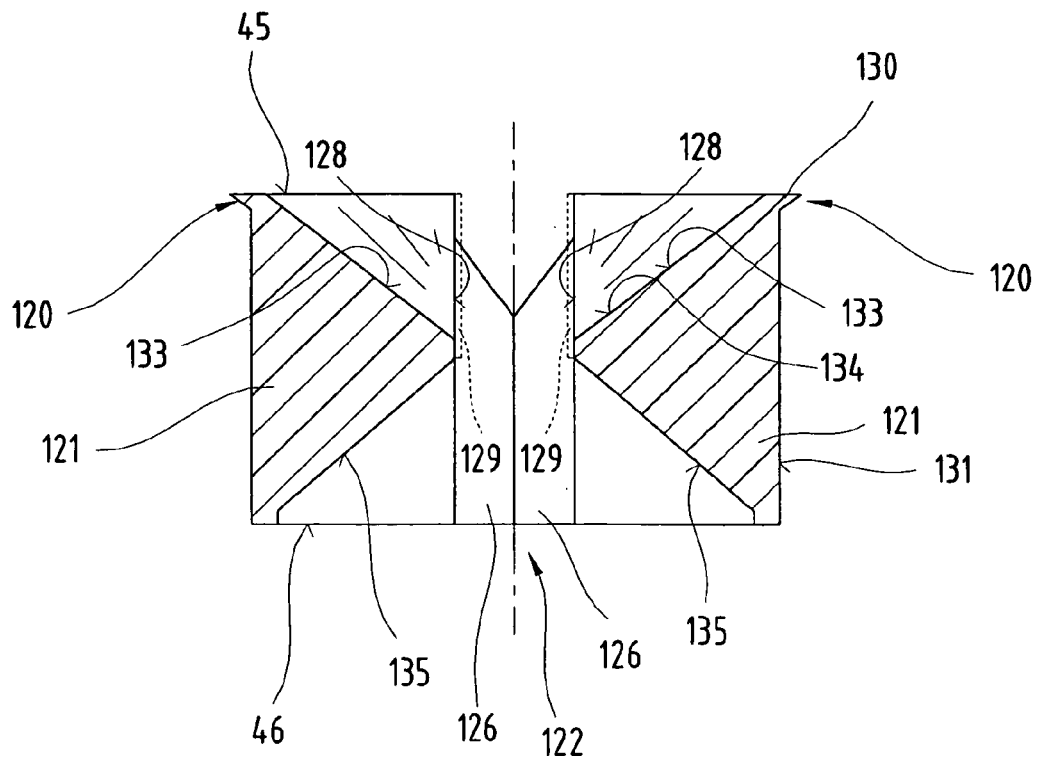
FIG. 22 is a side view in section showing the separating mechanism illustrated in FIGS. 20 and 21 along line XXII—XXII indicated in FIG. 21.

FIGS. 20 to 22 illustrated another container system 1 for a mixture 2 of the type described above, the same parts being denoted by the same reference numbers as those used for FIGS. 1 to 19 above. To avoid unnecessary repetition, reference may be made to the description of FIGS. 1 to 19 above.

The container system again consists of the container receptacle 5, which has a container receptacle chamber 117 with an internal wall 18 bounding and enclosing it. The container receptacle 5 also has two ends 5, 6 spaced at a distance apart from one another in the direction of its longitudinal axis 15, at least one of which has an orifice. In the region of the internal wall 118, an internal dimension 14 of the container receptacle chamber 117 in the region of the first end 6 in a plane 16 perpendicular to the longitudinal axis 15 is bigger than the internal dimension 18 in the region of the other end 7 in the plane 17 parallel therewith in the same spatial direction, tapering in an angled or conical arrangement depending on the reduction in the dimension of the receptacle chamber 117. At one of the open ends 6, 7 at least, is a closing device 9, not illustrated in detail, which can be opened and which is used to close the container receptacle 5 as necessary.

The separating mechanism 11 is again inserted in the receptacle chamber 117 or interior 10 and, depending on the design of the sealing stopper of the closing device abutting with the internal wall 118, is spaced apart from the open end in this case in the direction of the other end 7 by a pre-definable extent from the end face 19. The separating mechanism 11 is bounded by the two ends regions 45, 46 spaced apart from one another in the direction of the longitudinal axis 15. A flow passage 119, which can be closed off, is provided between these mutually spaced end regions 45, 46. At least one sealing device 120 is also provided between the separating mechanism 11 and the container receptacle 5, in particular its internal wall 118.

The separating mechanism 11 has at least one and in the example illustrated here two components 121, which are forced against at least certain regions of the internal wall 118 of the container receptacle 5 by at least one pressing element 122 in the initial position.

The two components 121 forming the separating mechanism 111 in this instance form a more or less semicircular surface as viewed in the direction of the longitudinal axis 15, and in the operating position, in other words in the position sealing the flow passage 119, which in this example is between the mutually facing regions of the components 121, providing a tight and in particular fluid-tight seal. This closing movement of the flow passage 119 may be achieved by means of the decrease from the larger internal dimension 14 of the container receptacle chamber 17 to the smaller internal dimension 18 in the region of the other end 7, as described above, dimensioned so that once displaced from the initial position or starting position into its operating position, the separating mechanism 11 is securely fixed in position without the heavier medium being inadvertently able to pass into the lighter medium during the centrifugation process or after it has been completed.

The pressing element 121 disposed between the components 121 causes a radially directed pressing force on the two components in the direction of the internal wall 118, so that the sealing device 120 is already brought into contact via the periphery with at least certain regions of the internal wall 118 during the initial position.

In the initial position, the container receptacle chamber 117 disposed between the separating mechanism 11 and the other end 7 can be evacuated via the flow passage 119. After evacuation, the closing device 9, in particular the sealing stopper 22, is then inserted in the receptacle chamber 117 of the container receptacle 5 and stored in this state. This container system 1 is now ready for receiving bodily fluids, pieces of tissue or tissue cultures, in particular blood, for which purpose the sealing stopper is pierced with a needle and the container system 1 can be filled as a result of the vacuum pressure prevailing in the container receptacle chamber 117.

The internal dimension 14 and an internal periphery of an envelope of the container receptacle chamber 117 in the first plane 16 is bigger than an external dimension 123 and an external periphery of an envelope of the component(s) 121 in its or their operating position and in the same spatial direction. This ensures that a flow of the mixture to be introduced into the container receptacle chamber can be established through the flow passage 119 in the initial position. After filling, the centrifugation processes described above is run and the mixture 2 separated into the two media 3, 4. To this end, the flow passage 119 is disposed between the ends 6, 7 of the container receptacle n5 in the region of the separating mechanism 11 in the initial position. As a result of the centrifugal force acting on the separating mechanism 11, the separating mechanism 11 is moved from the initial position towards the operating position at a distance apart, where an internal dimension 124 or an internal periphery of an envelope of the receptacle chamber 117 is the same as or smaller than the external envelope of the component(s) 121 and the external dimension 123 in the same position.

The component or components 121 of the separating mechanism 11 automatically seal off the flow passages 119 in the operating position, due to the dimensional decrease of the receptacle chamber 117 in the manner of a control curve. This being the case, the decrease of the internal dimension 14 to the internal dimension 124 in the region of the operating position may be uniform or constant. However, it would also be possible for one part-section of the distance between the initial position and the operating position to be cylindrical and the remaining part-section to taper in a conical or angled arrangement.

In order to produce a guaranteed displacement motion to the separating mechanism 11 whilst the centrifugal force is being applied, the selected density will depend on the density values of the individual media to be separated 3, 4. If the mixture 2 is blood, the density of the separating mechanism will be in excess of 1.05 $g/cm^3$. Depending on the level of centrifugal force selected for the centrifugation process, the separating mechanism 11 may have a density of between 1.5 $g/cm^3$ and 3.5 $g/cm^3$, preferably between 2.0 $g/cm^3$ and 2.5 $g/cm^3$.

As may be seen most clearly from FIGS. 21 and 22, the separating mechanism 11 in the embodiment illustrated as an example here consists of two components 121 and pressure elements 122 disposed centrally between them. Depending on the size of the external dimension 123 of the separating mechanism 11, however, several of these components 121 may be provided. The essential factor, however, is that the components 121 should also move at the same relative displacement speed by reference to the container receptacle 5 during the overall displacement motion relative to the container, so that a common displacement will occur during the centrifugation process, thereby ensuring that a sealing and in particular fluid-tight closure is obtained between the two mutually separated container receptacle chambers 117 in the container receptacle 5 in the operating position.

In order to produce as uniform a pressing force as possible, a respective pressing element 122 is provided for the components 121 of the separating mechanism 11 on either side of a plane of symmetry 125 extending through the longitudinal axis and perpendicular to the flow passage 119 and hence disposed between the mutually facing regions of the components 121. To place the components 121 in a sealing position in the operating position, the two components 121 forming the separating mechanism 11 can be displaced relative to one another in a plane perpendicular to the longitudinal axis 15, as a result of which they always assume the same position relative to the container receptacle 5 and can therefore also be displaced simultaneously.

By providing the pressing element or elements 122, the components 121 of the separating mechanism 11 are always held in their relative mutual position and are therefore joined to one another in displacement. The pressing elements 122 are advantageously symmetrically disposed relative to the longitudinal axis 15 and may be provided in the form of mutually joined resilient webs 126 that are V-shaped as viewed in the direction of the longitudinal axis 15 and converging in the direction of the longitudinal axis 15. The component 121 or components 121 and the pressing element 122 or pressing elements 122 is/are preferably made from the same type of material, so that the separating mechanism 11 can be made in a single production process for example, which might be an injection moulding process in an injection moulding tool for example.

To obtain a sealing abutment of the mutually facing regions of the components 121, a matching recess 127 may be provided, as indicated by broke lines in FIG. 21. Consequently, the individual resilient webs 126 can be snapped into the recess or recesses 127 as they are moved from the initial position into the operating position, thereby securing a flat abutment between the components 121 in order to seal off the flow passage 119. The resilient webs 126 forming the pressing element 122 are mutually joined in displacement to the components 121 on the mutually facing end regions and to the components 121 on the end regions remote therefrom. As a result of the V-shaped design, a pressing force is applied in the direction remote from the flow passage 119, starting from the pressing elements 122, the purpose of which is to permit a flow through the flow passage 119 until the components 121 sit in mutual abutment in the region of the mutually facing regions. This is necessary in order to fill the receptacle chamber 117 on the one hand and to allow through the media being separated during the centrifugation process on the other.

The mutually facing regions of the components 121 form planar abutting sealing surfaces 128, preferably in the end region 45. In addition, however, it would also be possible to provide a sealing arrangement 129 between the components 121 of the separating mechanism 11, in the area of the end region 45 directed towards the first end 6 of the container receptacle 5, to seal off the flow passage or passages 119. This sealing arrangement 129 is indicated in broken lines in the region of the sealing surfaces 128 in FIG. 22 and may be provided in a range of different embodiments. It might consist of interlocking or overlapping sealing lips, flap seals, etc.

The sealing device 120 disposed between the separating mechanism 11 and the internal wall 118 of the container receptacle chamber 117 should be arranged in the area of the end region 45 facing the first end 6 of the container receptacle 5, to prevent any mixture 2 starting to accumulate at the uppermost end of the separating mechanism 11 between the components 121 and the internal wall 118 at this early stage, which could subsequently cause the media to mix again having been separated. This would be the case, for example, if the sealing device 120 were arranged at a distance apart from the first end region 45 in the direction towards the other end region 46, which would mean that both constituents of the mixture would be able to penetrate this intermediate space during the filling process and could not then be emptied throughout the entire centrifugation process and also not separated, which would mean that partial quantities of both constituents would be left in the receptacle chamber 17 between the separating mechanism 11 and the closing device 9, which in our example would lead to contamination of the lighter medium.

The sealing device 120 is preferably provided in the form of at least one sealing lip 130 extending around at least an external periphery of the component 121, projecting radially outwards from the component 121 in the direction remote from the longitudinal axis 15. Due to the fact that the sealing lip 130 is elastically deformable to a certain extent, certain manufacturing tolerances can be compensated, in particular dimensional differences, between the components 121 and the container. The essential factor is that the sealing lip 130 provides a completely tight seal and in particular a fluid-tight seal for the region between the separating mechanism 11 and the internal wall 118 of the receptacle chamber 117 in the operating position, whatever the situation.

The component or components 121 provided between the mutually spaced apart end regions 45, 46 may be provided in the form of two components 121, each of which is a half-cylinder, for example, with the sealing lip 130 projecting out from the external periphery.

As an alternative to the above, however, it would also be possible for the components 121 to be provided in a region co-operating with the internal wall 118 of the container receptacle 5 by means of a section of a hollow cylinder or hollow truncated cone, which would enable a saving to be made on material. If only a hollow cylinder or hollow truncated cone is used, attention should be paid to the layout of the sealing surfaces 128 to be formed between the components 121, so that the flow passage 119 is automatically closed off in the mutually abutting position.

As described above, the sealing lip 130 projects out from the components 121, as a result of which the external dimension can be smaller than the internal wall 118 bounding the container receptacle chamber 17 across the entire displacement path. In order to prevent the separating mechanism 11 from jamming or tilting during the displacement process, it is of advantage to provide several support elements 132 on the components 121, distributed around the external periphery thereof and an external surface 131 projecting in the direction remote from the longitudinal axis 15. These support elements 132 are preferably distributed symmetrically relative to the longitudinal axis 15, around the external periphery on the external surface 131 and may be provided in the form of webs disposed parallel with the longitudinal axis 15, for example. However, these support elements 132 may also be provided around the external surface 131 in the form of nubs, spherical projections, etc., which may be distributed in any layout around the external surface 131.

In order to improve flow conditions between the mutually spaced apart end regions 45, 46 and prevent dead volumes, the components 121 preferably have conical sections 133 in the area of the first end region 45 directed towards the first end of the container receptacle 5 and in the direction of the longitudinal axis 15, with a baffle surface 134 tapering towards the other end region 46. It is also of advantage if the components 121 are provided with an inflow surface 135 in the area of the second end region 46 directed towards the other end 7 of the container receptacle 5 extending in the direction of the longitudinal axis 15 and at an angle towards the first end region 45.

This will enable the mixture to flow into the receptacle chamber 117 unhindered during the filling process and on towards the other end 7 of the container receptacle 5, also being guided by the peripheral regions, in other words from the area of the internal walls 118, in the direction of the flow passage 119. The inclined inflow surfaces 135 additionally prevent the lighter medium from penetrating the flow passage 119 during the separation process and again prevent the occurrence of any dead volumes.

Figure 23:
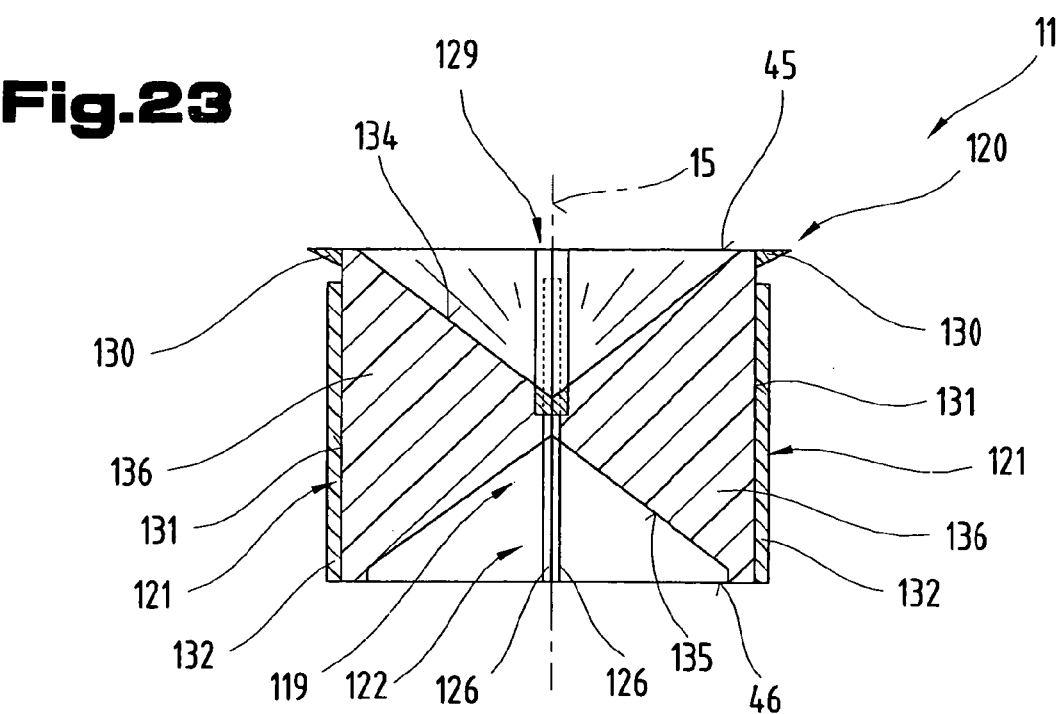
FIG. 23 is a simplified, schematic diagram in section, showing a side view of another embodiment of a separating mechanism proposed by the invention in the position in which the flow passage is closed.

FIG. 23 illustrates another embodiment of the separating mechanism 11, which may also be construed as an independent embodiment, the same parts being denoted by the same reference numbers as those used for the preceding FIGS. 1 to 22. As the separating mechanism 11 illustrated here differs from the one illustrated in FIGS. 20 to 22 in only a few respects, reference may be made to the more detailed description above.

Again in this embodiment, the separating mechanism 11 is made up of several, preferably two components 121, which are moved in displacement with one another by the pressing element or elements 122 in the form of resilient webs 126. The two components 121 are also illustrated in a sealing position in the region of the flow passage 119. In order to improve the variation in density of the entire separating mechanism 11, the component or components 121 of the separating mechanism 11 in this embodiment are provided respectively in the form of a support body 136 with the sealing device 120 and/or sealing system 129 arranged thereon. In this instance, it is of advantage if different materials are used to make the support body 136 and the sealing device 120 and/or sealing system 129.

The support body 136 should have a higher density than the sealing device 120 and/or the sealing system 129 and optionally a higher modulus of elasticity. Consequently, using a support body 136 of the same volume, a higher weight is obtained using a higher-density material, which ensures that the displacing motion will still be reliable at a lower centrifugal force.

The sealing device 120 or sealing system 129 may therefore be made from a silicone rubber, pharmaceutical rubber, bromobutyl rubber, rubber, a gel, a thermoplastic elastomer (TPE), thermoplastic polyurethane (TPU) or another elastomeric plastic, and the support body 136 may be made from a material selected from the group consisting of polyethylene terephthalate (PET), polypropylene (PP), polyethylene (PE), polystyrene (PS), high-density polyethylene (PE-HD), acrylonitrile butadiene styrene copolymers (ABS), thermoplastic elastomers (TPE), thermoplastic polyurethane (TPU), ultra-high molecular polyethylene with a very high molar weight (UHMW-PE), polycarbonate (PC), polyamide (PA), polyoxymethylene (POM) and any other thermoplastic synthetic material or optionally a combination of these. The sealing system 129 may but need not necessarily be provided. Naturally, it would also be possible to use other and different materials for the sealing system 129 between the support bodies 136. The sealing lips 130 forming the sealing device 120 project out from the external face 13 at the side remote from the longitudinal axis 15 to secure a better seal and provide the sealing closure between the separating mechanism 11 and the internal wall 118 on termination of the centrifugation process. The other seal of the of the flow passage 119 between the components 121, in particular the support bodies 136, is provided by means of the sealing system 129 assigned to the first end region 45, which is schematically illustrated in a simplified format in the form of sealing strips. This sealing system 129 may in turn be provided in various designs and may be provided in the area of the flow passage in regions of the components 121 directed towards the sealing abutment.

The pressure element or elements 122 are again provided between the components 121, and for the sake of simplicity are shown as mutually abutting resilient webs 126. The pressure element 122 may naturally also be provided in any other form, although care must be taken to ensure that a sufficient opposing pressing force is applied to the individual components 121 on the one hand and a sealed closure of the flow passage 119 is obtained in the operating position on the other.

As also illustrated in this drawing, to stabilise the position during the displacement process, at least certain regions of the external surface 131 may be provided with support elements 132 projecting out from them, for example in the form of lengthwise webs or ribs or spherical stubs distributed around the periphery in order to support the internal wall 118. These support elements 132 stand proud of the external surface 131 by dimensions such that they sit against the internal wall 118 during the entire displacement process until reaching the operating position, and the sealing device 120, in particular the sealing lip 130, also projects outwards from the envelope line around the support elements 132 in the direction of the internal wall. As a result of their elasticity, the sealing lips 130 are deformed on the side remote from the separating mechanism, in the projecting region where the support elements 132 stand proud of the envelope line. The displacement force needed in order to effect the movement from the initial position into the operating position can be fixed depending on the size of the projection.

If the support element 132 is provided in the form of a continuous web, it should be noted that it must be made separately from the sealing lip 130 under all circumstances in order to ensure that the sealing lip is able to move unhindered during deformation and produce a sealing abutment on the internal wall 118. An external envelope end in the region of the support elements 132 will be smaller than the external diameter of the sealing lips 130 of the sealing device 120 in the non-deformed state. Since the sealing lips 130 already project beyond the envelope formed by the support elements 132 in the initial position, the sealing lips will deform when a pressing force is applied by the pressing element or elements 122. The extent of the deformation will depend on how far out the sealing lips 130 project beyond the envelope formed by the support elements 132. The separating mechanism 11 is fixed in its seating in the region of the operating position by the abutment of the individual support elements 132 on the internal wall 118 of the container receptacle 5 on the one hand and by the deformed sealing lips 130 in the sealing position relative to the internal wall 118 on the other.

Figure 24:
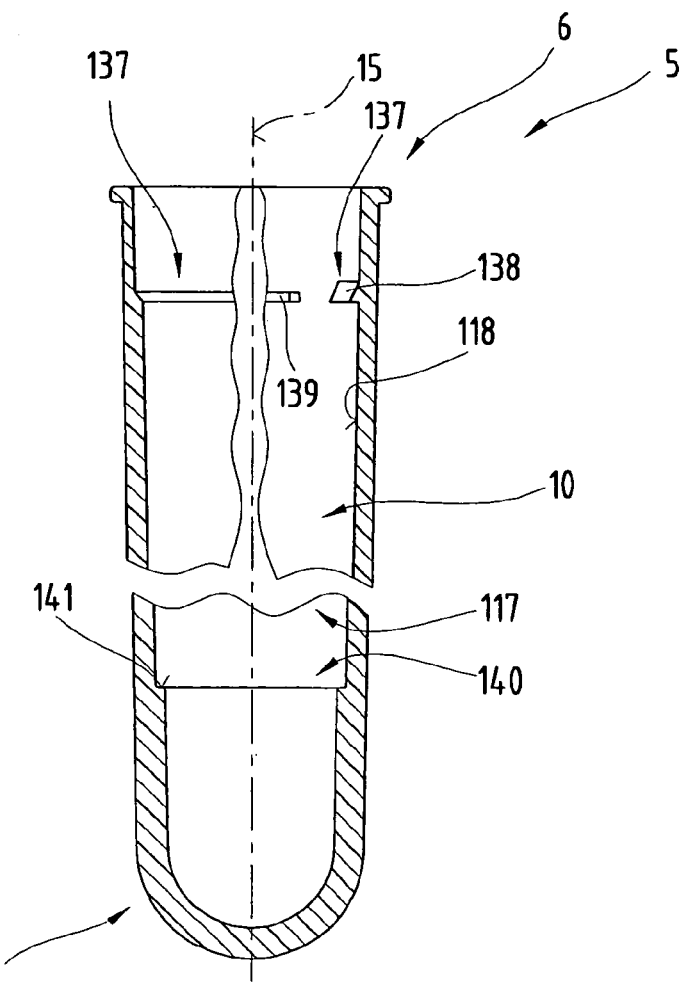
FIG. 24 is a simplified, schematic diagram in section, showing a side view of another embodiment of the container system proposed by the invention with the sealing device and separating mechanism removed.

FIG. 24 provides a schematic illustration of various possible embodiments of the container receptacle 5 in a single drawing, all of which can be used in any combination with one another. For the sake of clarity, the separating mechanism 11 and closing device 9 have been left out of the drawing.

Various embodiments of retaining mechanisms 137 are shown in the region adjacent to the end 6 of the container receptacle 5 where the separating mechanism 11 is to be inserted in the interior 10 or receptacle chamber 117 in the initial position. In the right-hand part of the drawing, the retaining mechanism 137 is provided in the form of at least one shoulder 138 projecting out from the periphery of the internal wall 118 in the direction towards the longitudinal axis 15 and/or by at least one web 139 projecting out from at least certain regions of the periphery of the internal wall 118 in the direction towards the longitudinal axis 15. Both the shoulder 138 and/or the web 139 may extend around only certain regions or alternatively may extend continuously around the entire periphery of the internal wall 118.

The left-hand upper region of FIG. 24 shows a different embodiment of the retaining mechanism 137, in this case in the form a reduction in the internal dimension 14 of the receptacle chamber 117. This reduction can be achieved by providing the container receptacle 5 with the normal wall thickness of the container starting from the end 6 of the container receptacle 5 as far as the retaining mechanism 137 and then making the wall thickness larger from the retaining mechanism 137 in the direction towards the other end 7, so that the increase in wall thickness forms a step in the internal wall 118 extending in the direction towards the longitudinal axis 15. Alternatively, another option is to select the standard wall thickness of the container receptacle 5 for the area between the initial position and the other end 7 and make the wall thickness slimmer only in the region between the initial position and the end 6 of the container receptacle 5, which in this case is open.

Depending on the design of the retaining mechanism 137, the separating mechanism 11 will be positioned when a pre-definable centrifugal force is reached, at which the retaining forces are overcome and the separating mechanism 11 is moved relative to the container receptacle 5 until it reaches the operating position.

In order to ensure that the separating mechanism 11 is correctly positioned and its relative position fixed in the region of the operating position, the retaining mechanism 137 may be provided between the container receptacle 5 and the separating mechanism 11 in the form of a recess, not illustrated, which extends continuously around the internal periphery of the internal wall 118 and set back into it.

In order to ensure that the separating mechanism 11 is correctly positioned and its position fixed in the region of the operating position, a positioning mechanism 140 may be provided between the container receptacle 5 and the separating mechanism 11. This positioning mechanism 140 may be provided by reducing the internal dimension 124 of the receptacle chamber 117 and providing an abutment surface 141 perpendicular to the longitudinal axis 15. Both the other end region 46 of the separating mechanism 11 and its component 121 or alternatively the sealing device 120 disposed in the first end region 45, in particular the sealing lips 130, may sit on this abutment surface 141. This will provide a sealing and in particular fluid-tight closure between the media separated from one another at the end of the centrifugation process and will do so even over a longer period of storage.

The container receptacle 5 illustrated here has a reduction in the interior 10 starting from the initial position as far as the operating position, as described above, and this constitutes the control curve for the automatic closure of the flow passage or passages 119 in the region of the separating mechanism 11.

The taper provided on the container receptacle 5 in its interior 10 or the receptacle chamber 117 between the two planes 16, 17 spaced apart from one another may be between 0.1° and 3.0°, preferably between 0.6° and 0.8°.

Figure 25:
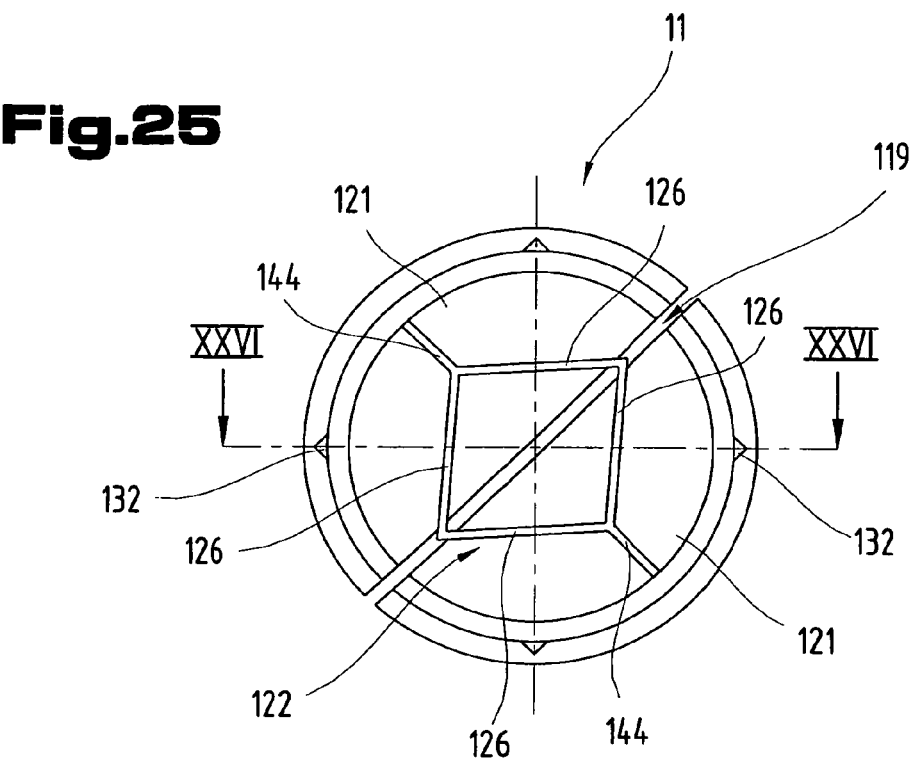
FIG. 25 is a simplified, schematic diagram showing a different separating mechanism proposed by the invention, viewed from underneath.
Figure 26:
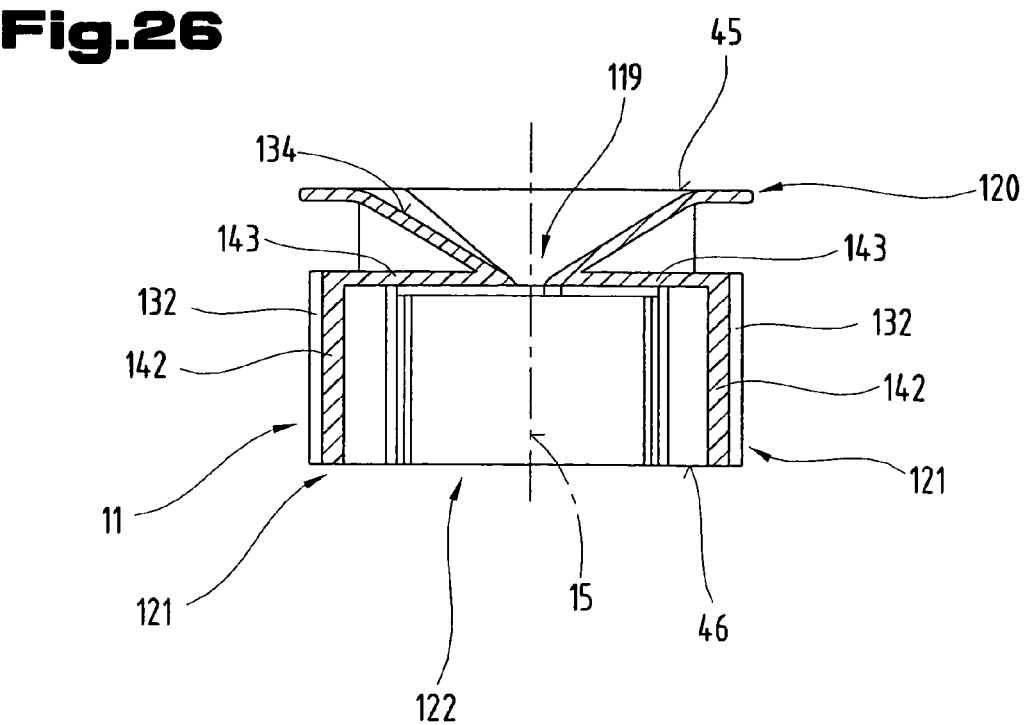
FIG. 26 is a view of the separating mechanism illustrated in FIG. 25, seen in section along line XXVI—XXVI indicated in FIG. 25.

FIGS. 25 and 26 illustrate another embodiment of the separating mechanism 11 with the pressing element 122, which may also be construed as an independent embodiment, the same parts being denoted by the same reference numbers as those used for FIGS. 1 to 24 above. To avoid unnecessary repetition, reference may be made to the detailed description of FIGS. 1 to 24 above.

The separating mechanism 11 again consists of the components 121 and the flow passage 119 is formed between the mutually facing components. The sealing device 120 is again disposed in the first end region 45 in the area of the external periphery of the components 121 in order to seal the receptacle chambers 117 to be separated and may correspond to the embodiments described above in connection with FIGS. 20 to 23. The same also applies to the design of the conical section forming the baffle surface 134, which tapers from the peripheral regions in the direction towards the longitudinal axis 15 and opens into the flow passage 119.

Starting from the other end region 46 of the separating mechanism 11, the components 121 are respectively provided in the form of hollow cylinder segments 142—in this particular case two components extending essentially in a half-circle. In the region of the converging baffle surfaces 134, end wall parts 143 are provided in order to join the hollow cylinder segments 142, which extend in a plane substantially perpendicular to the longitudinal axis 15.

The pressing element 122 is in turn provided by means of resilient webs 126 joined to one another, disposed in a parallelogram arrangement relative to one another in the direction of the longitudinal axis 15. The resilient webs 126 associated with the oppositely lying components 121 are joined to one another in the region of the flow passage and are supported in a plane offset from the flow passage 119 by approximately 90°, optionally by means of retaining webs 144, on the oppositely lying hollow cylinder segments 142.

Since the resilient webs 126 are symmetrically distributed relative to the flow passage 119 and due to the fact that the resilient webs 126 are supported against the hollow cylinder segments 142 offset at an angle thereto, the components 121 are pressed against the respective oppositely lying walls 118 of the container receptacle 5 in an essentially symmetrical arrangement relative to the flow passage 119 during for the entire time they are disposed in the container receptacle 5.

Figure 27:
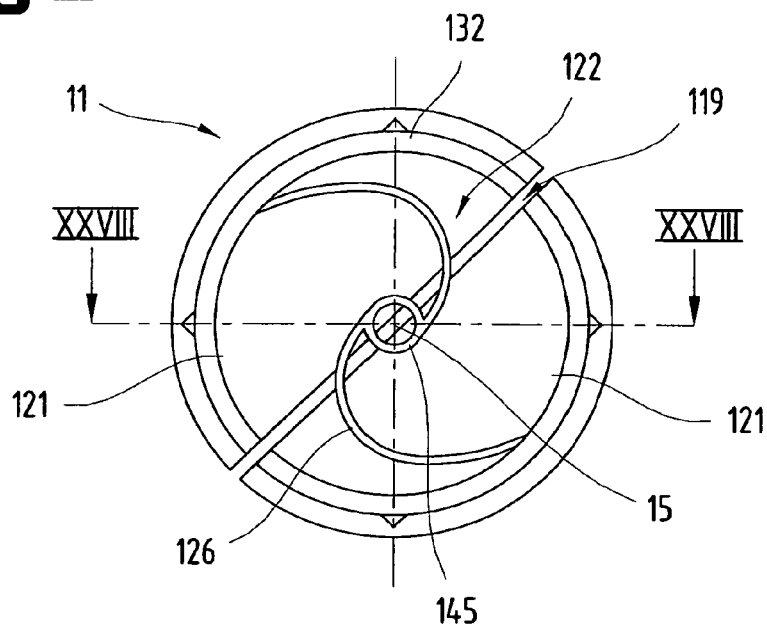
FIG. 27 is a simplified, schematic diagram of another separating mechanism proposed by the invention, viewed from underneath.
Figure 28:
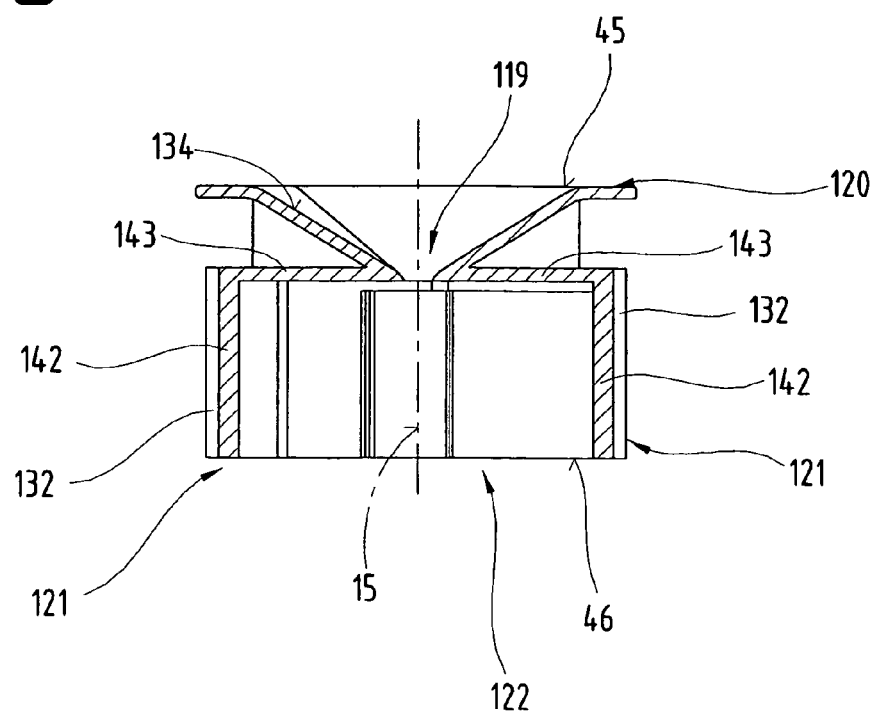
FIG. 28 is a view of the separating mechanism illustrated in FIG. 27, seen in section along line XXVIII—XXVIII indicated in FIG. 27.

FIGS. 27 and 28 illustrate another possible embodiment and layout of the pressing element 122 for the components 121 forming the separating mechanism 11, the design of the components 121 being the same as that described in connection with FIGS. 25 and 26 above. Reference may be made to this description to avoid unnecessary repetition.

The pressing element 122 is again disposed between the hollow cylinder segments 142, centrally relative to the longitudinal axis 15 and between the components 121, whilst the resilient webs 126 have a longitudinal extension which curves in the direction towards the longitudinal axis 15 and the counteracting curvature produces the requisite pressing force on the components 121 in the direction substantially perpendicular to the flow passage 119. A connecting part 145 is provided in the region of the longitudinal axis 15, being circular in this case, to which the mutually facing ends of the resilient webs 126 are joined in a plane substantially perpendicular to the flow passage 119. The other ends of the arcuately curved resilient webs 126 are joined to the internal face of the hollow cylinder segments 142 in essentially the same plane.

In the case of the pressing elements 122 described in connection with FIGS. 25 to 28, the resilient webs 126 are each joined at oppositely lying regions only, by reference to the flow passage 119, and are so exclusively to the hollow cylinder segments 142, in order to be able to transmit the springing action to the components 121 unobstructed. The resilient webs 126 must not be joined to the end wall parts 143 under any circumstances.

Figure 29:
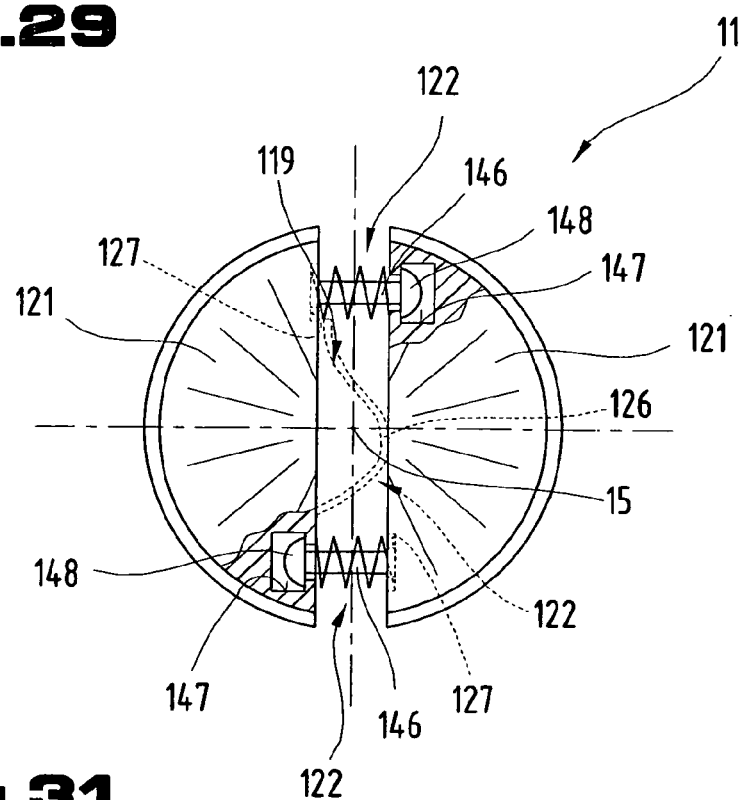
FIG. 29 is a simplified, schematic diagram in partial section, showing a plan view of a different embodiment of the separating mechanism proposed by the invention.

FIG. 29 is a simplified diagram illustrating another possible layout of the pressing elements 122 between the components 121, the same parts again being denoted by the same reference numbers as those used for FIGS. 1 to 28 above.

In the embodiment illustrated as an example here, the individual pressing elements 122 are provided in the form of helical springs, for example, supported on the mutually facing regions of the components 121. In order to support them in the mutually facing wall parts of the components 121 in the position in which the flow passage 119 is closed off and sealed, matching recesses 127 may be set back into at least one of these surfaces.

To facilitate assembly and ensure that the individual components 121 are reciprocally retained relative to one another, at least one guide part 146 is provided in the region of the pressing elements 122 and extends from at least one of the components 121 in the direction towards the oppositely lying component 121, locating in a seating orifice 147 set back in the other component 121, as illustrated. It is also of advantage to provide a retaining projection 148 in the end region of the guide part 126 extending into the seating orifice 147, the external dimension of which extends beyond the guide part 146 in the radial direction. In the radial direction towards the guide part 146, the seating orifice 147 has a bigger dimension in the region of the retaining projection 148 than in the region immediately adjoining the flow passage 119. In this region, the dimension of the seating orifice 147 is essentially the same as that of the guide part 146. The retaining projection 148, which is bigger in diameter, is elastically deformed as it is pushed into the first part of the seating orifice 148 and then snaps into seating orifice 147 which is of bigger dimensions in order to accommodate the retaining projection 148. In co-operation with the pressing element 122, the two components 121 are pushed apart in the region of the flow passage 119 so that the retaining projection 148 cooperating with the smaller seating orifice 147 provides a restriction and prevents the components 121 from falling part.

Another possibility as an alternative to providing the pressing element or elements 122 in the region of the guide parts 146 as illustrated here, is to retain a separate pressing element 122 on one of the components 121, as indicated in a simplified format by broken lines.

This pressing element 122 has a curved longitudinal extension and is provided in the form of a resilient web 126, which is joined to one of the components 121 at an end region and extends towards the oppositely lying component 121 in a curved arrangement in the region of the flow passage 119, as viewed in the direction towards the longitudinal axis 15. By providing the guide parts 146 and the seating orifice 147 co-operating with them, the components 121 can be mutually aligned and the pressing mechanism is again disposed between the two mutually facing regions of the components 121 but separated from the guide parts 146 in order to keep them mutually spaced apart and form the flow passage 119.

FIG. 30 illustrates another embodiment of the container system 1 and this embodiment consists of the container receptacle 5 and a container 149 which is inserted in the interior 10. The closing device 9 and the separating mechanism 11 have been left out of the drawing in order to retain clarity.

The container system 1 may be used with any of the embodiments of the separating mechanism 11 in which the closure of the flow passage 119 and the connecting orifice 44 is based on the principle of a reduction in the internal dimension of the receptacle chamber 117 starting from the initial position and extending as far as the operating position.

At its end 6, which in this case is open, the container receptacle 5 extends beyond an end face 150 of the container 149 by a pre-definable distance, which is selected so that the end face 150 serves as the retaining mechanism 137 described above for the separating mechanism 11 to be inserted in the receptacle chamber 117. The internal dimension 14 in the region of the end face 150 is selected specifically to form the flow passage 119 and connecting orifice 44 in the region of the separating mechanism 11 as a ratio of the separating mechanism 11 and its components 121, such that the mixture 2 is able to pass into the receptacle chamber 117 during filling.

In the region of the operating position of the separating mechanism 11, the container 149 has an internal dimension 123, which is smaller than the internal dimension 14 in the region of the end face 150. This means, for example, that using the same external dimensions for the container receptacle 5, the receptacle chamber 117 can be made with different sizes in the region of the container 149, for example, and the internal dimensions 14, 123 and 18 can be simultaneously specifically selected relative to one another so as to fix the point at which the separating mechanism 11 is in the operating position relative to the container receptacle 5. The design of the mutually facing external and internal faces of the container receptacle 5 and container 149 as well as the selection of materials may be taken from patent specifications EP 0 735 921 B1, AT 402 365 B and U.S. Pat. No. 5,871,700 A.

Figure 31:
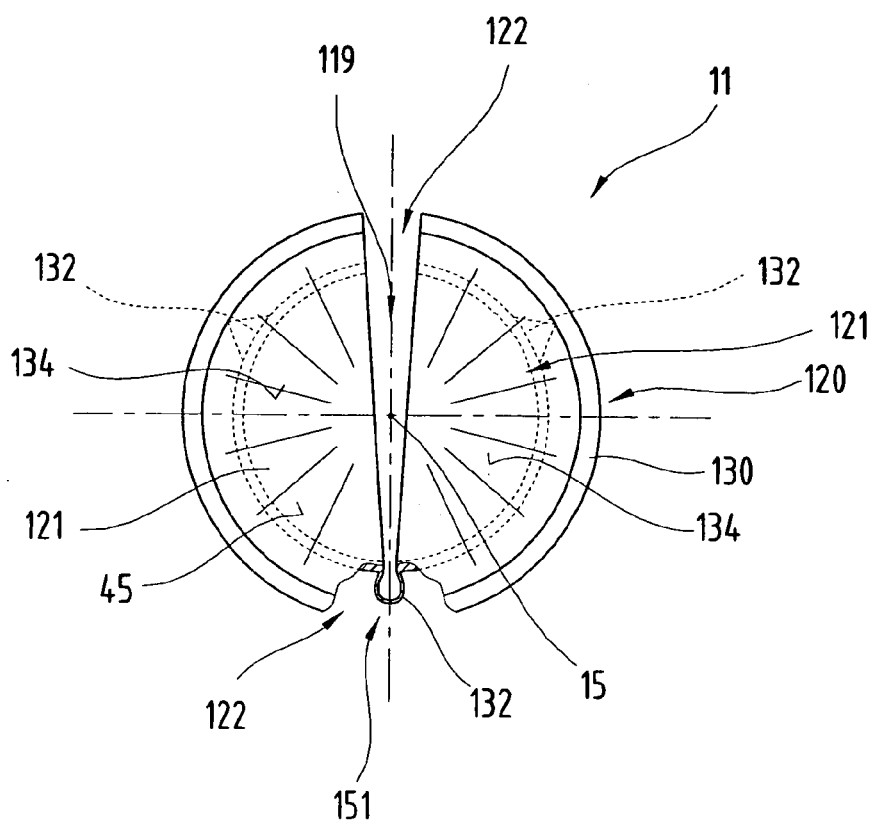
FIG. 31 is a simplified, schematic diagram showing a plan view in partial section of another embodiment of the separating mechanism proposed by the invention.

FIG. 31 shows another possible embodiment of the separating mechanism 11, which may also be construed as an independent embodiment, incorporating the components 121. To avoid unnecessary repetition, reference may be made to the description relating to FIGS. 1 to 30 above, the same parts being denoted by the same reference numbers.

The flow passage 119 in this example of an embodiment is also formed by the mutually facing regions of the components 121 and the sealing device 120 with the sealing lip is provided in the first end region 45, preferably extending continuously around the periphery of the individual components 121. The design of the baffle surface 134 in the first end region 45 may be the same as the embodiments described in connection with FIGS. 20 to 29.

The two components 121 are pivotably joined to one another by a hinge joint 151 in an end region of the flow passage 119 and this hinge joint may simultaneously serve as one of the supporting elements 132, for example. Other support elements 132 are also provided in the region of the external periphery, as illustrated in simplified format. The design of the support elements 132 and their distribution around the periphery may be freely selected to suit respective requirements.

The hinge joint 151 may also simultaneously act as the pressing element 122, in which case the components 121 forming the flow passage 119 will always be pressed against the internal wall 118 as they are inserted in the container system 1.

However, it would also be possible to provide one or more additional pressing elements 122 in the end region of the flow passage 119 lying opposite the hinge joint 151, as indicated by broken lines. This will enable another selectively directed force to be applied to the mutually facing components 121 so that the flow passage 119 can be held open to permit a flow in the initial position until such time as the sealing and operating position is reached.

The hinge joint 151 may be made from a material that is the same as that of the component 121 or different. This hinge joint 151 is preferably made in the same work process as the components 121 are made, which will obviate the need for subsequent joining processes to assemble the separating mechanism 11. It also reduces the complexity of the assembly process when inserting the separating mechanism 11 in the container system 1 because although the separating mechanism 11 may be made up of several parts, it can be inserted in the receptacle chamber 117 in a single piece.

The key feature of the embodiments described immediately above with reference to FIGS. 20 to 31 is that the container receptacle 5 and the container 149 taper in their interior 10 or receptacle chamber 117 between the two planes 16, 17 by between approximately 0.1° and 3.0°, preferably between 0.6° and 0.8°. This could also vary by plus/minus 10%. The container receptacle 5 and/or the container 149 and/or the component 121 and/or the sealing device 120 or sealing system 129 and/or the pressing element 122 may be made from a fluid-tight, in particular water-tight and optionally also gas-tight plastic. This plastic is selected from the group consisting of polyethylene terephthalate (PET), polypropylene (PP), polyethylene (PE), polystyrene (PS), high-density polyethylene (PE-HD), acrylonitrile butadiene styrene copolymer (ABS), thermoplastic elastomers (TPE), thermoplastic polyurethane (TPU), ultra-high molecular polyethylene with a very high molecular weight (PE-UHMW), polycarbonate (PC), polyamide (PA), polyoxymethylene (POM), silicone rubber, pharmaceutical rubber, bromobutyl rubber, rubber, a gel or a combination selected from these.

The component or components 121 forming the base body are preferably made from materials selected from the group consisting of PE-UHMW, PC, PA, POM or other thermoplastic plastics. The pressing element 122 may be made from the softer material used for the sealing device 120 or sealing system 129 for example, or alternatively from the same material as that used for the base body and its components 121. However, it would also be possible to use the materials specified in connection with FIGS. 1 to 19.

Certain regions of the component 121 or alternatively only part-regions of it may be provided with a coating, in which case this could be a coating of silicone, for example. The interior 10 or receptacle chamber 117 of the container receptacle 5 may be evacuated to a pressure below atmospheric pressure before fitting and closing the closing device 9.

For the sake of good order, it should finally be pointed out that in order to provide a clearer understanding of the container receptacle, the closing device and the separating mechanism 11, they and their constituent parts are illustrated to a certain extent out of proportion and/or on an enlarged scale and/or on a reduced scale.

The independent solutions proposed by the invention and the underlying objectives may be found in the description.

Above all, the individual embodiments of the invention illustrated in FIGS. 1, 2, 3, 4; 5; 6; 7, 8; 9 to 13; 14 to 16; 17, 18; 19; 20, 21, 22; 23; 24; 25, 26; 27, 28; 29; 30; 31 may be construed as independent solutions proposed by the invention. The related objectives and solutions proposed by the invention may be found in the detailed descriptions of these drawings.

LIST OF REFERENCE NUMBERS

1 Container system
2 Mixture
3 Medium
4 Medium
5 Container receptacle
6 End
7 End
8 End wall
9 Closing device
10 Interior
11 Separating mechanism
12 Container wall
13 Wall thickness
14 Dimension
15 Longitudinal axis
16 Plane
17 Plane
18 Dimension
19 End face
20 Cap
21 Sealing device
22 Sealing stopper
23 Cap casing
24 Coupling part
25 Coupling part
26 Coupling part
27 Coupling part
28 Coupling mechanism
29 Extension
30 Extension
31 Retaining ring
32 Shoulder
33 Sealing surface
34 Sealing surface
35 Recess
36 Opening
37 Guide extension
38 Guide extension
39 Guide web
40 Guide web
41 Base body
42 Abutment surface
43 Coating
44 Connecting orifice
45 End region
46 End region
47 Recess
48 Insert part
49 Distance
50 Plane
50a Plane
51 Dimension
52 Dimension
53 Cone angle
54 Gap
55 Arc length
56 Gap face
57 Gap face
58 Width
59 Depth
60 Retaining mechanism
61 Web
62 Length
63 Recess
64 Casing part
65 Orifice
66 Wall part
67 Rib
68 Groove
69 Displacement path
70 Dimension
71 Plane
72 Dimension
73 Face
74 External face
75 Sealing device 76 Sealing lip
77 Dimension
78 Dimension
79 Support body
80 Catch element
81 Retaining mechanism
82 Shoulder
83 Abutment surface
84 Sealing surface
85 Envelope
86 Width
87 Dimension
88 Joining surface
89 Recess
90 Width
91 Thickness
92 Shoulder part
93 Stop ring
94 Part
95 Recess
96 Recess
97 Wall thickness
98 Boundary surface
99 Retaining mechanism
100 Catch element
101 Width
102 Dimension
103 Projection
104 Flow passage
105 Diameter
106 Abutment surface
107 Guide element
108 Projection
109 Height
110 Orifice width
111 Dimension
112 Recess
113 Recess
114 Total length
115 Part-length
116 Part-length
117 Receptacle chamber
118 Internal wall
119 Flow passage
120 Sealing device
121 Component
122 Pressing element
123 Dimension
124 Dimension
125 Plane of symmetry
126 Resilient web
127 Recess
128 Sealing surface
129 Sealing system
130 Sealing lip
131 External surface
132 Support element
133 Cone portion
134 Baffle surface
135 Inflow surface
136 Support body
137 Retaining mechanism
138 Shoulder
139 Web
140 Positioning mechanism
141 Abutment surface
142 Hollow cylinder segment
143 End wall part
144 Retaining web
145 Connecting part
146 Guide part
147 Seating orifice
148 Retaining projection
149 Container
150 End face
151 Hinge joint

The invention claimed is:

1. Separating mechanism (11) for inserting in a receptacle chamber (117) of a container receptacle (5) of a container system (1), having at least one component (121) with a sealing device (120) which can be directed towards an internal wall (118) of the container receptacle (5) and having first end region (45) and second end region (46) spaced at a distance apart from one another in the direction of a longitudinal axis (15) of the container receptacle between which a flow passage (119) extends, characterized in that the components (121) can be applied against certain regions of the internal wall (118) of the container receptacle (5) by at least one pressing element (122) and, in the initial position, the flow passage (119) is established between the adjacently disposed components (121) spaced at a distance apart from one another by the pressing element (122), the pressing elements having resilient webs (126) which are V-shaped as viewed in the direction of the longitudinal axis (15) and converge in the direction towards the longitudinal axis (15).

2. Separating mechanism as claimed in claim 1, characterized in that the separating mechanism has a density greater than 1.05 g/cm$^3$.

3. Separating mechanism as claimed in claim 1, characterized in that the components (121) can be displaced relative to one another in a plane perpendicular to the longitudinal axis (15).

4. Separating mechanism as claimed in claim 1, characterized in that the components (121) are held in their position relative to one another by the pressing element (122).

5. Separating mechanism as claimed in claim 1, characterized in that an appropriate recess (127) is provided for the pressing element (122) in at least one of the mutually facing regions of the components (121).

6. Separating mechanism as claimed in claim 1, characterized in that a sealing system (129) for sealing off the flow passage or passages (119) is provided between the components (121) of the separating mechanism (11) in the area of the first end region (45) directed towards a first end (6) of the container receptacle (5).

7. Separating mechanism as claimed in claim 1, characterized in that the sealing device (120) is disposed between the separating mechanism (11) and the receptacle chamber (117) in the area of the first end region (45) directed towards a first end (6) of the container receptacle (5).

8. Separating mechanism as claimed in claim 1, characterized in that the sealing device (120) is provided in the form of at least one sealing lip (130) extending continuously around the periphery of the component (121), and sections of the sealing lips (130) adjacent to the flow passage (119) locate with one another or overlap at least when the separating mechanism (11) is in the operating position.

9. Separating mechanism as claimed in claim 1, characterized in that several support elements (132) are provided on the components (121) projecting out from an external periphery and an external surface (131) thereof in the direction remote from the longitudinal axis (15), the support elements (132) being webs aligned parallel with the longitudinal axis (15).

10. Separating mechanism as claimed in claim 1, characterized in that the components (121) have baffle surfaces (134) disposed in the area of the first end region (45) directed towards a first end (6) of the container receptacle (5) tapering in the direction towards the longitudinal axis (15) and as far as the second end region (46).

11. Separating mechanism as claimed in claim 1, characterized in that the components (121) have an inflow surface (135) in the area of the second end region (46) directed towards a second end (7) of the container receptacle (5), which extend in the direction towards the longitudinal axis (15) and are inclined relative to the first end region (45).

12. Separating mechanism as claimed in claim 1, characterized in that at least one guide part (146) projects out from one of the components (121) between mutually facing regions of the components (121) and a seating orifice (147) co-operating therewith is provided on the other component (121) for the guide part (146).

13. Separating mechanism as claimed in claim 1, characterized in that the components (121) of the separating mechanism (11) are respectively provided in the form of a support body (136) and the sealing device (120) and/or sealing system (129) disposed thereon.

14. Container system (1) with a container receptacle (5) which bounds a receptacle chamber (117) with an internal wall (118) and having first end (6) and second end (7) spaced at a distance apart in the direction of the longitudinal axis (15) of the container receptacle, at least one of which has an orifice, and in the region of the internal wall (118), an internal dimension (14) of the receptacle chamber (117) in the region of the first end (6) in a first plane (16) perpendicular to the longitudinal axis (15) is bigger than an internal dimension (18) in the region of the second end (7) in a second plane (17) parallel therewith in the same spatial direction, having at least one closing device (9) for the first and second end (6, 7) of the container receptacle (5), with a separating mechanism (11) inserted in the receptacle chamber (117) and the separating mechanism being displaceable from an initial position to an operating position spaced apart in the direction towards the second end (7), characterized in that the separating mechanism (11) is designed as claimed in claim 1 and has at least one component (121) which is applied by at least one pressing element (122) against certain regions of the internal wall (118) of the container receptacle (5), and the internal dimension (14) and an internal periphery of an envelope line of the receptacle chamber (117) in the first plane (16) is bigger than an external dimension (123) and an external periphery of an envelope line of the component (121) in its operating position in the same spatial direction, and a flow passage (119) is established between the first and second ends (6, 7) of the container receptacle (5) in the region of the separating mechanism (11) in the initial position, and an internal dimension (124) and an internal periphery of an envelope line of the receptacle chamber (117) in the region of the operating position of the separating mechanism (11) is the same as or smaller than the external periphery of an envelope line of the component (121) in the same position, and the component (121) of the separating mechanism (11) automatically seals off the flow passage or passages (119) in the operating position, and a retaining mechanism (137) is provided for the separating mechanism (11), the retaining mechanism (137) being a groove-shaped recess extending continuously around the periphery of the internal wall (118).

15. Container system as claimed in claim 14, characterized in that a positioning mechanism (140) is provided between the container receptacle (5) and the separating mechanism (11) in the region of the operating position, which is provided in the form of a reduction in the internal dimension (124) of the receptacle chamber (117) and forms an abutment surface (141) essentially perpendicular to the longitudinal axis (15).

16. Container system as claimed in claim 14, characterized in that a taper of the container receptacle (5) in its interior (10) or its receptacle chamber (117) between the first and second planes (16, 17) spaced apart along the longitudinal axis of the container receptacle is between 0.1° and 3.0°.

17. Container system as claimed in claim 14, characterized in that the container receptacle (5) and/or the container (149) and/or the component (121) and/or the sealing device (120) or sealing arrangement (129) and/or the pressing element (122) is or are made from a fluid-tight plastic.

18. Container system as claimed in claim 17, characterized in that the plastic is selected from the group consisting of polyethylene terephthalate (PET), polypropylene (PP)1 polyethylene (PE), polystyrene (PS), high-density polyethylene (PE-HD), acrylonitrile butadiene styrene copolymers (ABS), thermoplastic elastomers (TPE), thermoplastic polyurethane (TPU), ultra-high molecular polyethylene with a very high molecular weight (PE-UHMW), polycarbonate (PC), polyamide (PA), polyoxymethylene (POM), silicone rubber, pharmaceutical rubber, bromobutyl rubber, rubber, a gel and a combination thereof.

19. Separating mechanism (11) for inserting in a receptacle chamber (117) of a container receptacle (5) of a container system (1), having at least one component (121) with a sealing device (120) which can be directed towards an internal wall (118) of the container receptacle (5) and having first end region (45) and second end region (46) spaced at a distance apart from one another in the direction of a longitudinal axis (15) of the container receptacle between which a flow passage (119) extends, characterized in that the components (121) can be applied against certain regions of the internal wall (118) of the container receptacle (5) by at least one pressing element (122) and, in the initial position, the flow passage (119) is established between the adjacently disposed components (121) spaced at a distance apart from one another by the pressing element (122), the pressing elements having resilient webs (126) which are V-shaped as viewed in the direction of the longitudinal axis (15) and converge in the direction remote from the longitudinal axis (15).

20. Separating mechanism as claimed in claim 19, characterized in that the separating mechanism has a density greater than $1.05 \text{ g/cm}^3$.

21. Separating mechanism as claimed in claim 19, characterized in that the components (121) can be displaced relative to one another in a plane perpendicular to the longitudinal axis (15).

22. Separating mechanism as claimed in claim 19, characterized in that the components (121) are held in their position relative to one another by the pressing element (122).

23. Separating mechanism as claimed in claim 19, characterized in that an appropriate recess (127) is provided for the pressing element (122) in at least one of the mutually facing regions of the components (121).

24. Separating mechanism as claimed in claim 19, characterized in that a sealing system (129) for sealing off the flow passage or passages (119) is provided between the components (121) of the separating mechanism (11) in the area of the first end region (45) directed towards a first end (6) of the container receptacle (5).

25. Separating mechanism as claimed in claim 19, characterized in that the sealing device (120) is disposed between the separating mechanism (11) and the receptacle chamber (117) in the area of the first end region (45) directed towards a first end (6) of the container receptacle (5).

26. Separating mechanism as claimed in claim 19, characterized in that the sealing device (120) is provided in the form of at least one sealing lip (130) extending continuously around the periphery of the component (121), and sections of the sealing lips (130) adjacent to the flow passage (119) locate with one another or overlap at least when the separating mechanism (11) is in the operating position.

27. Separating mechanism as claimed in claim 19, characterized in that several support elements (132) are provided on the components (121) projecting out from an external periphery and an external surface (131) thereof in the direction remote from the longitudinal axis (15), the support elements (132) being webs aligned parallel with the longitudinal axis (15).

28. Separating mechanism as claimed in claim 19, characterized in that the components (121) have baffle surfaces (134) disposed in the area of the first end region (45) directed towards a first end (6) of the container receptacle (5) tapering in the direction towards the longitudinal axis (15) and as far as the second end region (46).

29. Separating mechanism as claimed in claim 19, characterized in that the components (121) have an inflow surface (135) in the area of the second end region (46) directed towards a second end (7) of the container receptacle (5), which extend in the direction towards the longitudinal axis (15) and are inclined relative to the first end region (45).

30. Separating mechanism as claimed in claim 19, characterized in that at least one guide part (146) projects out from one of the components (121) between mutually facing regions of the components (121) and a seating orifice (147) co-operating therewith is provided on the other component (121) for the guide part (146).

31. Separating mechanism as claimed in claim 19, characterized in that the components (121) of the separating mechanism (11) are respectively provided in the form of a support body (136) and the sealing device (120) and/or sealing system (129) disposed thereon.

32. Separating mechanism (11) for inserting in a receptacle chamber (117) of a container receptacle (5) of a container system (1), having at least one component (121) with a sealing device (120) which can be directed towards an internal wall (118) of the container receptacle (5) and having first end region (45) and second end region (46) spaced at a distance apart from one another in the direction of a longitudinal axis (15) of the container receptacle between which a flow passage (119) extends, characterized in that the components (121) can be applied against certain regions of the internal wall (118) of the container receptacle (5) by at least one pressing element (122) and, in the initial position, the flow passage (119) is established between the adjacently disposed components (121) spaced at a distance apart from one another by the pressing element (122), and a recess (127) is provided for the pressing element (121) in at least one of facing regions of the components (121).

33. Separating mechanism as claimed in claim 32, characterized in that the separating mechanism has a density greater than 1.05 g/cm³.

34. Separating mechanism as claimed in claim 32, characterized in that the components (121) can be displaced relative to one another in a plane perpendicular to the longitudinal axis (15).

35. Separating mechanism as claimed in claim 32, characterized in that the components (121) are held in their position relative to one another by the pressing element (122).

36. Separating mechanism as claimed in claim 32, characterized in that an appropriate recess (127) is provided for the pressing element (122) in at least one of the mutually facing regions of the components (121).

37. Separating mechanism as claimed in claim 32, characterized in that a sealing system (129) for sealing off the flow passage or passages (119) is provided between the components (121) of the separating mechanism (11) in the area of the first end region (45) directed towards a first end (6) of the container receptacle (5).

38. Separating mechanism as claimed in claim 32, characterized in that the sealing device (120) is disposed between the separating mechanism (11) and the receptacle chamber (117) in the area of the first end region (45) directed towards a first end (6) of the container receptacle (5).

39. Separating mechanism as claimed in claim 32, characterized in that the sealing device (120) is provided in he form of at least one sealing lip (130) extending continuously around the periphery of the component (121), and sections of the sealing lips (130) adjacent to the flow passage (119) locate with one another or overlap at least when the separating mechanism (11) is in the operating position.

40. Separating mechanism as claimed in claim 32, characterized in that several support elements (132) are provided on the components (121) projecting out from an external periphery and an external surface (131) thereof in the direction remote from the longitudinal axis (15), the support elements (132) being webs aligned parallel with the longitudinal axis (15).

41. Separating mechanism as claimed in claim 32, characterized in that the components (121) have baffle surfaces (134) disposed in the area of the first end region (45) directed towards a first end (6) of the container receptacle (5) tapering in the direction towards the longitudinal axis (15) and as far as the second end region (46).

42. Separating mechanism as claimed in claim 32, characterized in that the components (121) have an inflow surface (135) in the area of the second end region (46) directed towards a second end (7) of the container receptacle (5), which extend in the direction towards the longitudinal axis (15) and are inclined relative to the first end region (45).

43. Separating mechanism as claimed in claim 32, characterized in that at least one guide part (146) projects out from one of the components (121) between mutually facing regions of the components (121) and a seating orifice (147) co-operating therewith is provided on the other component (121) for the guide part (146).

44. Separating mechanism as claimed in claim 32, characterized in that the components (121) of the separating mechanism (11) are respectively provided in the form of a support body (136) and the sealing device (120) and/or sealing system (129) disposed thereon.

* * * * *